US008492332B2

(12) United States Patent
Paukshto et al.

(10) Patent No.: US 8,492,332 B2
(45) Date of Patent: Jul. 23, 2013

(54) ORIENTED COLLAGEN-BASED MATERIALS, FILMS AND METHODS OF MAKING SAME

(75) Inventors: Mikhail Vitoldovich Paukshto, Foster City, CA (US); David Harwood McMurtry, Felton, CA (US); Yuri Alexandrovich Bobrov, Menlo Park, CA (US); Eric Eugene Sabelman, Menlo Park, CA (US)

(73) Assignee: Fibralign Corporation, Sunnyvale, CA (US)

( * ) Notice: Subject to any disclaimer, the term of this patent is extended or adjusted under 35 U.S.C. 154(b) by 1177 days.

(21) Appl. No.: 12/106,214

(22) Filed: Apr. 18, 2008

(65) Prior Publication Data

US 2009/0069893 A1 Mar. 12, 2009

Related U.S. Application Data

(60) Provisional application No. 60/912,925, filed on Apr. 19, 2007.

(51) Int. Cl.
*A61K 38/00* (2006.01)
*C07K 14/00* (2006.01)

(52) U.S. Cl.
USPC .............................................. 514/2; 530/300

(58) Field of Classification Search
None
See application file for complete search history.

(56) References Cited

U.S. PATENT DOCUMENTS

| | | | |
|---|---|---|---|
| 4,544,516 A | 10/1985 | Hughes et al. | |
| 4,869,200 A | 9/1989 | Euverard | |
| 4,902,508 A * | 2/1990 | Badylak et al. | 424/423 |
| 5,171,273 A | 12/1992 | Silver et al. | |
| 5,744,545 A | 4/1998 | Rhee et al. | |
| 5,922,028 A * | 7/1999 | Plouhar et al. | 623/23.72 |
| 6,544,762 B1 | 4/2003 | Tranquillo et al. | |
| 6,592,623 B1 | 7/2003 | Bowlin et al. | |
| 6,737,053 B1 | 5/2004 | Goh et al. | |
| 6,824,716 B2 | 11/2004 | Liao et al. | |
| 6,887,488 B2 | 5/2005 | Cui et al. | |
| 7,048,963 B2 | 5/2006 | Braithwaite et al. | |
| 7,338,517 B2 | 3/2008 | Yost et al. | |
| 7,354,627 B2 | 4/2008 | Pedrozo et al. | |
| 2003/0139806 A1 | 7/2003 | Haverkost et al. | |
| 2005/0009178 A1 | 1/2005 | Yost et al. | |
| 2005/0019488 A1 | 1/2005 | Braithwaite et al. | |
| 2005/0240261 A1 | 10/2005 | Rakos et al. | |
| 2005/0267231 A1 | 12/2005 | Pavlin | |
| 2006/0198827 A1 | 9/2006 | Levenberg | |
| 2007/0041952 A1 | 2/2007 | Guilak et al. | |
| 2008/0115724 A1 | 5/2008 | McMurtry et al. | |
| 2008/0147199 A1 | 6/2008 | Yost et al. | |
| 2008/0254091 A1 | 10/2008 | Lee et al. | |
| 2010/0036098 A1 * | 2/2010 | Paukshto et al. | 530/356 |
| 2011/0151563 A1 * | 6/2011 | Paukshto et al. | 435/395 |

FOREIGN PATENT DOCUMENTS

| | | |
|---|---|---|
| EP | 0 518 697 A2 | 12/1992 |
| JP | 2004-148014 | 5/2004 |
| WO | WO 84/00548 | 2/1984 |
| WO | WO 99/47188 | 9/1999 |
| WO | WO 00/61045 | 10/2000 |
| WO | WO 03/020316 | 3/2003 |
| WO | WO 2004/050134 | 6/2004 |
| WO | WO 2005/003300 | 1/2005 |
| WO | WO 2005/081699 | 9/2005 |
| WO | WO 2006/136817 | 12/2006 |
| WO | WO 2007/028078 | 3/2007 |
| WO | WO 2007/038601 | 4/2007 |
| WO | WO 2008/034854 | 3/2008 |
| WO | WO 2008/070166 | 6/2008 |
| WO | WO 2009/064437 | 5/2009 |
| WO | WO 2010/019625 | 2/2010 |

OTHER PUBLICATIONS

Ledet et al., "A pilot study to evaluate the effectiveness of small intestinal submucosa used to repair spinal ligaments in the goat", The Spine Journal 2: 188-196 (2002).*
McPherson and Badylak, "Characterization of Fibronectin Derived from Porcine Small Intestinal Submucosa", Tissue Engineering, vol. 4, No. 1, 75-83 (1998).*
European Search Report from European Application No. EP08746355, dated Jun. 4, 2010, 8 pages.
Martin et al., "Behavior of cells on highly organized and reconstituted collagen matices," Molecular Biology of The Cell, Bethesda MS USA, vol. 19, No. supp. Dec. 13, 2008, p. 42.
Besseau, L. et al., "Production of Ordered Collagen Matrices for Three-Dimensional Cell Culture," Biomaterials, 23, 2002, pp. 27-36.
Cisneros, D. et al., "Creating Ultrathin Nanoscopic Collagen Matrices for Biological and Biotechnological Applications", Wiley InterScience, 2007, vol. 3, No. 6, pp. 956-963.
Cowin, S., "Do Liquid Crystal-Like Flow Processors Occur in the Supramolecular Assembly of Biological Tissues?", J. Non-Newtonian Fluid Mech. 119, 2004, pp. 155-162.

(Continued)

*Primary Examiner* — Anand Desai
(74) *Attorney, Agent, or Firm* — Nixon Peabody LLP

(57) ABSTRACT

In general, the present invention is related to collagen compositions and thin films, and to methods of making and using the same. In some embodiments, the present invention is directed to "uniaxial pattern" or "linear pattern" collagen materials, compositions and thin films, and methods of making.

49 Claims, 10 Drawing Sheets

OTHER PUBLICATIONS

Eglin, D. et al., "Type I Collagen, a Versatile Liquid Crystal Biological Template for Silica Structuration from Nano-to Microscopic Scales," The Royal Society of Chemistry 2005, 1, pp. 129-131.

Evans, H., et al. "Novel 3D Culture System for Study of Cardiac Myocyte Development," Am J. Physiol Heart Circ Physiol 285: 2003, H570-H578.

Fennell, L., et al., "Thin Crystal Film Polarizers," Asia Display/IDW '01, pp. 601-603.

Gobeaux, F., Cooperative Ordering of Collagen Triple Helices in the Dense State, Langmuir 2007, vol. 23, pp. 6411-6417.

Guo, C. et al., "Flow and Magnetic Field Induced Collagen Alignment", Biomaterials 28, 2007, pp. 1105-1114.

Knight, D. et al. "Biological Liquid Crystal Elastomers", Philosophical Transactions: Biological Sciences, vol. 357, No. 1418, Estomeric Proteins: Structures, Biomechanical Properties and Biological Roles. Feb. 28, 2002, pp. 155-163.

Martin, R. et al., "Liquid Crystalline Ordering of Procollagen as a Determinant of Three-Dimensional Extrqacellular Matrix Architecture", J. Mol. Biol. 301: 2000, pp. 11-17.

Ng, C. P., et al., "Fibroblast Alignment Under Interstitial Fluid Flow Using a Novel 3-D Tissue Culture Model", Am J. Physical Heart Circ. Physiol 284: Jan. 16, 2003, pp. H1771-H1777.

Paukshto, M., et al., "Optics of Sheard Liquid-Crystal Polarizer Based on Aqueous Dispersion of Dichroic-Dye Nano-Aggregates", Journal of the SID, 13/9, 2005, pp. 765-772.

Tan, W. et al. "Layer-by-Layer Microfluidics for Biomatic Three-Dimensional Structures", Biomaterials, 2004, vol. 25, pp. 1355-1364.

Yoshizato, K. et al., "In Vitro Orientation of Fibroblasts and Myoblasts on Aligned Collagen Film", Develop., Growth and Differ., 23 (2), 1981, pp. 175-184,1981.

Zhong, S. et al., "An Aligned Nanofibrous Collagen Scaffold by Electrospinning and its Effects on In Vitro Fibroblast Culture", Journal of Biomedical Materials Research Part A, 2006 Wiley Periodical, Inc., pp. 456-463.

International Search Report and Written Opinion for PCT/US2007/025037 dated Apr. 8, 2008.

Hansen, U., et al., "Material Properties of Biological Tissues Related to Joint Surgery," Current Orthopaedics, 2006, vol. 20, pp. 16-22.

International Search Report and Written Opinion for PCT/US2008/060919 dated Oct. 17, 2008.

Office Action in U.S. Appl. No. 11/951,324, mailed Sep. 7, 2011.

Notice of Allowance in U.S. Appl. No. 11/951,324, mailed Mar. 20, 2012.

Office Action in U.S. Appl. No. 12/539,563, mailed Jun. 7, 2012.

International Search Report and Written Opinion in PCT/US2009/053486, dated Mar. 26, 2010.

European Examination Report in Application No. EP 08746355.0, dated Mar. 31, 2011.

European Examination Report in Application No. EP 08746355.0, dated Sep. 5, 2011.

International Search Report and Written Opinion in PCT/US2011/051135, dated Apr. 26, 2012.

* cited by examiner

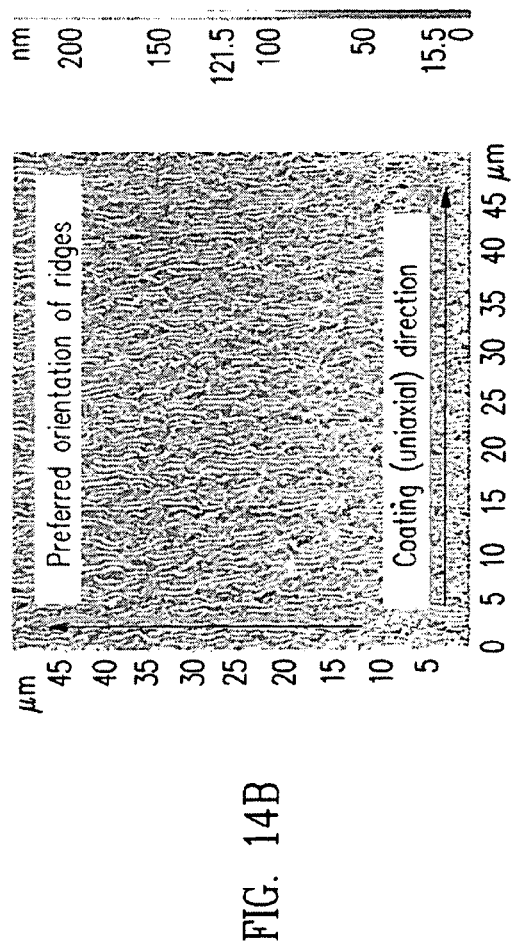
FIG. 14B
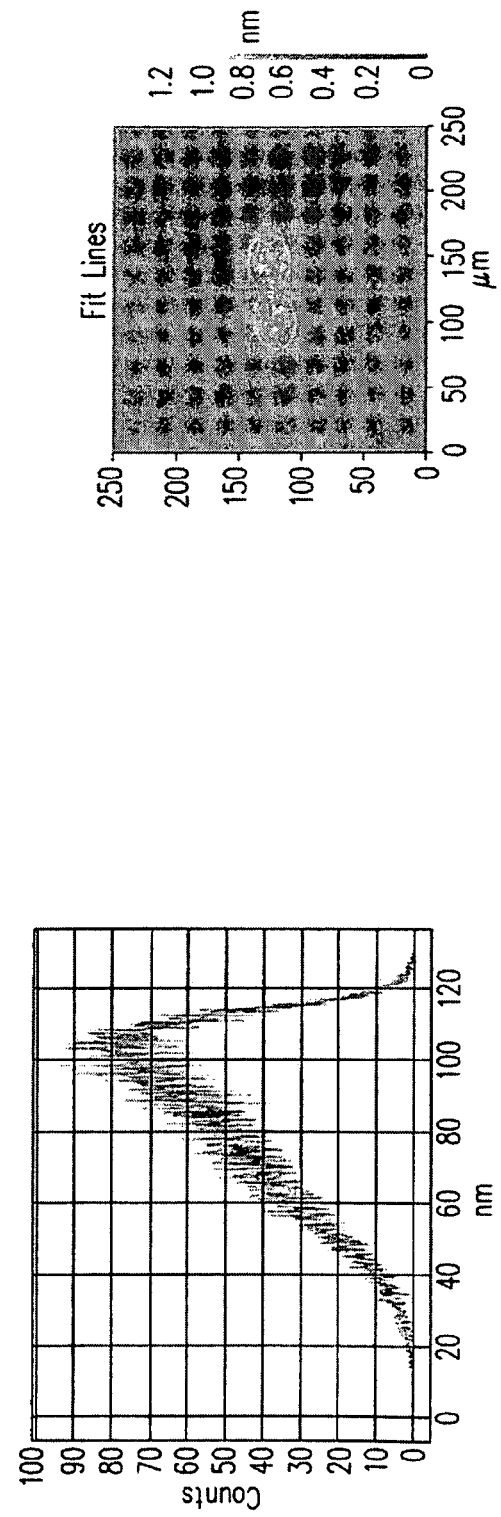
FIG. 14D
FIG. 14C

ORIENTED COLLAGEN-BASED MATERIALS, FILMS AND METHODS OF MAKING SAME

CROSS REFERENCE TO RELATED APPLICATIONS

This application claims the benefit of, and priority to, U.S. Provisional Patent Application Ser. No. 60/912,925 filed on Apr. 19, 2007, the entire disclosures of which is hereby incorporated by reference in its entirety.

FIELD OF THE INVENTION

In general, the present invention is related to collagen materials, compositions and films, and to methods of making and using the same. In some embodiments, the present invention is directed to "uniaxial pattern" or "linear pattern" collagen materials, compositions and thin films, and methods of making.

BACKGROUND OF THE INVENTION

Collagen is a common substrate for attachment-dependent mammalian cells, both in the living body and in vitro. Naturally, collagen is secreted by cells as long triple-helical monomer, which polymerizes spontaneously into fibrils and strands, which often have a preferential orientation essential to the function of tissues such as skin, bone and nerve. Cells, in turn, will orient themselves parallel a linear pattern (i.e. fibrils, ridges, or grooves) on the surface to which that are attached. During secretion and deposition as the extracellular matrix, the globular propeptides are cleaved by specific procollagen proteinases, triggering fibril formation, as illustrated in FIG. 1A as reported by M. J. Buehler, Proc Nati Acad Sci US 103, 12285-12290, 2006.

Oriented collagen differs from other cell-adhesion substrate in that linearity is inherent at the molecular level, rather a surface phenomenon. Homogeneous material may be textured or printed with attachment factors, but this topography lies in a two-dimensional plane. Other materials with molecular linearity (e.g. carbon nanotubes) do not have collagen's biocompatibility or capacity to interact with native biomolecules.

The property of linear molecular alignment is important for several reasons. For example, highly oriented collagen cell culture scaffold offers advantage at other ends of the cell differentiation pathway. Cells which remain undifferentiated after division are known as "stem cells" particularly if one of the daughter cells goes on to undergo differentiation (specialization and loss of capacity to generate undifferentiated daughter cells—top level in FIG. 1B. To maintain stem cells in their undifferentiated state while encouraging their proliferation, it requires an environment that protects the cell from physical factors that induce differentiation as well as controlling of chemical factors in the nutrient medium. For example, in the body, stem cells reside in niches such as bone marrow (hematopoietic stem cells) or glandular crypts; the stem cells never leave these habitats.

Collagen matrix in many biological systems has a liquid crystal structure. It is the natural state of the collagen, which provides a long-range orientation. Liquid crystal is a state of matter that is intermediate between the crystalline solid and the amorphous liquid. There are three basic phases of liquid crystals, known as smectic phase, nematic phase, and cholesteric phase as illustrated in FIGS. 2a-2c. FIG. 2a illustrates the smectic phase in which one-dimensional translational order, as well as orientational order exists. FIG. 2b illustrates the nematic phase in which only a long-range orientational order of the molecular axes exists. Cholesteric phase is also a nematic liquid type with molecular aggregates lie parallel to one another in each plane, but each plane is rotated by a constant angle from the next plane, as shown in FIG. 2c, FIG. 3, and FIGS. 4a-4b. The cholesteric phase is a chiral form of the nematic phase. Chiral describes a structural characteristic of a molecule that prevents it from being superposed upon its mirror image. The "twisted plywood model" shown in FIG. 3 is a model of the organization of molecules in a cholesteric structure. This model explains how typical series of arcing patterns observed in sections of cells and tissues result not from authentic curved filaments but originate from the successive molecular orientations found in the twisted plywood arrangement. The model is constructed as follows. The molecular directions are represented by parallel and equidistant straight lines on a series of rectangles, with the orientation of the lines rotating from one rectangle to the next by a small and constant angle. A periodicity is visible wherein each 180° rotation of the molecular directions corresponds to the half-cholesteric pitch P/2. The rotation is chosen to be left-handed, as has been found in all biological twisted materials studied so far. A cholesteric axis is defined by the left-hand rule, the closed first of the left hand indicating the progressive direction of twist and the extended thumb of the left hand pointing in the positive direction of the cholesteric axis. Directly visible on the oblique sides of the pyramid are what appear to be superposed series of parallel nested arcs. The concavities of the arcs are reversed on opposite sides of the model. In biological systems this particular geometry has often been described as twisted plywood. More, background information is provided in Cowin and Doty, Tissue Mechanics, Springer, 2007, herein is incorporated by reference in its entirety, especially page 289-339.

Two major types of twists are found in liquid crystals and their biological analogues and are defined by the disposition of the fibrillar elements either in parallel planes (planar twist) or coaxial cylinders (cylindrical twist) (see FIG. 4). The coaxial cylinders or cylindrical twist are also described as helicoidal. Collagen in the secondary osteons of bone tissue is observed to be in a helicoidal pattern as is cellulose in plant cell walls.

Collagen I can be deposited from solution by a variety of process including casting, lyophilization, electrospinning and other processes well known to one skilled in the art. In most of these procedures, collagen fibers of widely varying diameters and lengths from the micrometer range typical of conventional fibers down to the nanometer range are formed, which provides a mat of interlaced fibers having interstices and pores which provide a suitable foundation for anchoring cells. Owing to their small diameters, electrospun fibers possess very high surface-to-area ratios and are expected to display morphologies and material properties very different from their conventional counterparts occurring in nature. Belamie E. et al. J. Phys. Condens. Matter, 2006, 18, 115-129.

Another technique recently reported uses an inkjet printer capable of printing at high resolution by ejecting extremely small ink drops. This method was described in Nakamura M. et al., Tissue Engineering, 11:1658-1666 (2005) wherein the authors used a biocompatible inkjet head and investigated a feasibility of microseeding with living cells. Living cells are easily damaged by heat; therefore, they used an electrostatically driven inkjet system that was able to eject ink without generating significant heat. Bovine vascular endothelial cells were prepared and suspended in culture medium, and the cell suspension was used as "ink" and ejected onto culture disks.

Microscopic observation showed that the endothelial cells were situated in the ejected dots in the medium, and that the number of cells in each dot was dependent on the concentration of the cell suspension and ejection frequency chosen. After the ejected cells were incubated for a few hours, they adhered to the culture disks. While these developments have been made, this technique is limited and has not found widespread use. This technique is somewhat useful for delivering a material (e.g., cells) to a particular area but it cannot maintain and preserve the material's orientation.

All prior art methods of forming collagen films and matrices to date suffer from limitations as do the collagen-based materials formed there from. The main limitation is to maintain and preserve the native liquid crystal structure of collagen-like materials. For example, electrospinning and casting methods cannot preserve a long-range orientation. Collagen based films and matrices cannot mimic the native semi-crystalline structures of the extra-cellular matrix in the living biological systems. Other methods, like, for example, Langmuir-Blodgett method, have limited orientation and poor repeatability.

There are also attempts to produce collagen coating in the controlled matter. For example, U.S. Pat. No. 7,354,627 describes a method for preparing a protein polymer (such as collagen) material involves applying a form of energy such as electrical energy, gravitational energy, thermal energy, or chemical energy to a protein to cause the protein to assemble in a controlled arrangement to form a protein polymer material. U.S. Pat. No. 7,338,517 describes a method of producing a tubular tissue scaffold that comprises a tube wall which includes biopolymer fibrils that are aligned in a helical pattern around the longitudinal axis of the tube where the pitch of the helical pattern changes with the radial position in the tube wall. However, neither patent discloses a collagen layer that mimics the natural pattern and textual of collagen containing tissues.

Accordingly, there is significant need for new collagen-based materials mimicking native structures in living biological systems as well as the reliable and robust methods of producing such materials.

SUMMARY OF THE INVENTION

In general, the present invention is related to collagen compositions and thin films, and to methods of making and using the same. In some embodiments, the present invention is directed to oriented forms of collagen compositions and films with "uniaxial pattern," or "linear pattern" collagen compositions and thin films, and methods of making.

In one aspect, the present invention provides a monolayer or multilayer stack comprising a collagen layer, wherein the collagen layer comprises a plurality of fibrils exhibiting at least one preferred orientation, and the collagen layer has a uniaxial orientation. The fibrils may be characterized as "crimped" as described below. The collagen layer is formed by at least one type of collagen: e.g., I, II, III, V, or XI type collagen. In some embodiments the collagen may be chemically modified, or contain functional groups, and the like. Collagen may also include other peptides which behave similar to collagen, other similar bio-polymers, and the like.

In some embodiments, the plurality of crimped fibrils form a crimped fibril assembly, and the assembly comprises a plurality of ridges and valleys. In some embodiments, a plurality of crimped fibrils forms a repeatable elongated pattern consisting of an alternating series of ridges and valleys aligned in one preferred direction. In some embodiments, the plurality of crimped fibrils forms a repeatable elongated pattern consisting of an alternating series of ridges and valleys aligned in two preferred directions. In some embodiments, an alternating series of ridges and valleys have a pitch in range 100 nm-10 microns. In some embodiments, the ridges and valleys have width in the range of about 50 nm-5 microns and length in the range of about 100 nm-50 micron. In some embodiments, an alternating series of ridges and valleys have depth in the range of about 10 nm-1 micron. In some embodiments, the fibrils composed the ridges have an opposite direction in adjacent ridges. In some embodiments, an angle between two preferred directions of an alternating series of ridges and valleys is in the range of about 40-180 degree.

In some embodiments the angle between said uniaxial orientation and said preferred orientation is from 0 to 30 degrees. In some embodiments, the crimped fibrils display at least a partial translational order that correlates to the preferred orientation. In other embodiments, the crimped fibrils do not display at least a partial translational order that correlates to the preferred orientation.

In some embodiments, the crimped fibrils are helical-like fibrils, and wherein upper helixes of said helical-like fibers form said ridges and the lower helixes of said helical-like fibers form said valleys.

In some embodiments, the alignment angle variation of said crimped fibrils is less than ±15°. In some embodiments, there are at least 10 aligned crimped fibrils per 50 µm wide area of said collagen layer. In some embodiments, the cross section of said crimped fibrils is at least 30 nm. In some embodiments, the length of said crimped fibrils is at least 2 µm. In some embodiments, the average distance between adjacent ridges of said crimped fibril assembly is at least 100 nm. In some embodiments, the valley is about 10 to 1000 nm deep.

In some embodiments, the surface topography of a surface of said collagen layer exhibits an anisotropic Fourier image containing at least two petals. In some embodiments, the collagen layer produces anisotropic transmission diffraction pattern containing at least two petals when exposed to a collimated monochromatic light source having visible wavelength. In some embodiments, the collagen layer produces anisotropic reflective diffraction pattern containing at least two petals when exposed to a collimated monochromatic light source having visible wavelength.

In some embodiments, the surface topography of a surface of said collagen layer exhibits a frequency content containing at least two peaks. In some embodiments, the surface topography of a surface of the collagen layer exhibits a frequency content containing peaks at different frequencies when measured in substantially orthogonal directions. In some embodiments, the surface topography of a surface of the collagen layer exhibits a frequency content which produces a single maximum peak when measured substantially orthogonally to the preferred direction of the ridges.

In some embodiments, the ridges formed by the upper helixes of said helical-like fibers form an angle of at least 30 degree with said preferred orientation.

In some embodiments, the monolayer or multilayer stack comprises at least two collagen layers, wherein said uniaxial direction of each collagen layer may not necessarily be parallel to each another.

In some embodiments, the collagen layer further comprises pit-like formation at the boundaries of said crimped fibrils, and wherein said pit-like formations are filled with any one of: hydrogels, peptide based biomaterials, living tissue cell, and other bioactive materials like the incorporated ligands, encapsulated DNA, and growth factors, or the combinations thereof. In some embodiments, the monolayer or multilayer stack further comprises metal nanowires or carbon nanotubes.

In some embodiments, the monolayer or multilayer stack further comprises at least one functional layer. The functional layer is selected from any one of: lipid membrane, coagulant, living tissue cell layer, adhesion promotion layer, carrier layer, protective layer, delaminating promotion layer, or combinations thereof.

In some embodiments, the collagen layer is made by a liquid film applicator comprising: (i) at least two longitudinal side members having the form of parallel wedge-like rails with their bases occurring in the same plane as the substrate; (ii) a crossover member having the form of a bridge between said side members, wherein said crossover member has at least one flat face and is in contact with each said rail in at least one point; and (iii) a clamp system ensuring strict fixation of the bridge at any preset position on said rails, wherein said bridge can be moved along both said rails so that the flat face of said bridge makes a certain constant dihedral angle within 0-10 are minutes with the substrate plane and the gap between said flat face and said substrate plane has a width from 5 to 50 micron.

In some embodiments, the collagen layer is made by the steps of: conveying a collagen solution to a first plate and a second plate, wherein said second plate is held substantially parallel to said first plate at a gap width of 5 to 50 microns, and wherein the collagen solution is captured between said first and second plates; and moving said second plate parallel to said first plate to generate suitable shearing force on said collagen solution to produce said collagen layer, wherein said first plate being held stationary during said moving step, and wherein the direction of moving the second plate is the coating direction. In some embodiments, the coating direction is parallel to said uniaxial direction. In some embodiments, the concentration of said collagen solution is about 10 mg/ml-30 mg/ml. In some embodiments, the concentration of said collagen solution is at least 25 mg/ml. In some embodiments, the collagen solution presents in a nematic liquid crystal state. In some embodiments, the collagen layer is made by shearing of concentrated liquid collagen solution.

In some embodiments, the collagen layer is made by shearing of concentrated liquid collagen solution having at lease one of the collagen types of I, II, III, VI and XI, without limitation (including biologically or chemically modified collagen and the like) and optionally having one or more additives, such as for example without limitations an additive that is capable of promoting orientation or adhesion of said collagen. In some embodiments, the additive is ATP.

In some embodiments, the collagen layer further comprises cross-links by intra-monomeric disulfide bridges, glycosydic cross-links formed via nonenzymatic glycation, interstitial phosphate or sulfate cross-links, or covalent linkages promoted by the activity of the enzyme lysyl oxidase.

In another aspect, the present invention provides a method of making a monolayer or a multilayer stack having a collagen layer, said method comprising applying a shearing force to a collagen solution at a coating speed of about 10 to 100 mm per second. In some embodiments, the step of applying a shear force comprises conveying a collagen solution in the liquid phase through a slot-die type system at a coating speed of about 10 to 10000 mm per second. In some embodiments, the step of applying a shear force further comprises: conveying a collagen solution to a first plate and a second plate, wherein said second plate is held substantially parallel to said first plate at a gap width of 5 to 50 microns, and wherein said collagen solution is captured between said first and second plates; and moving said second plate parallel to said first plate to generate suitable shearing force on said collagen solution to produce said collagen layer, and wherein the direction of moving the second plate is the coating direction.

In another aspect, the present invention provides a three-dimensional matrix for use in three-dimensional cell culture, said matrix comprises a collagen layer, wherein said collagen layer comprises a plurality of crimped fibrils with at least one preferred orientation, and wherein said collagen layer has a uniaxial orientation. In some embodiments, the collagen layer is prepared by shearing and drying on an anistropic substrate with controlled pre-tilt angle. In some embodiments, the substrate is coated by anisotropic liquid crystal material. In some embodiments, the substrate is coated by polyamide like material with additional patterning and rubbing.

In yet another aspect, the present invention provides a method of making a monolayer or multilayer stack comprising a collagen layer, said method comprising the steps of: providing a first plate and a second plate, wherein said second plate is held substantially parallel to said first plate at a gap width of 5 to 50 microns, and wherein a collagen solution is captured between said first and second plates; and moving said second plate parallel to said first plate to generate suitable shearing force on said collagen solution to produce said collagen layer, wherein said first plate being held stationary during said moving step, and wherein the direction of moving the second plate is the coating direction.

In another aspect, the present invention provides a graft comprising a collagen layer, wherein said collagen layer comprises a plurality of crimped fibrils with at least one preferred orientation, and wherein said collagen layer has a uniaxial orientation. In some embodiments, the graft is a tendon graft or a ligament graft. In some embodiments, the graft further comprises a plurality of fibroblasts deposited on said collagen layer.

BRIEF DESCRIPTION OF THE DRAWINGS

The foregoing and other objects of the present invention will be apparent upon consideration of the following detailed description, taken in conjunction with the accompanying drawings, in which like reference characters refer to like parts throughout.

FIGS. 4a, 4a1, 4b, 4b1 depict structures reported by M. M. Giraud-Guille, Int. Rev. Cytol. 166:59-101 (1996) wherein (a) In a planar twist, equidistant straight lines are drawn on horizontal planes, and the direction of the lines rotates regularly from plane to plane. (a') In the conventional notation for a cholesteric geometry applied to a planar twist, lines represent molecules longitudinal to the drawing plane and dots represent molecules perpendicular to it; molecules in oblique position are represented by nails whose points are directed toward the observer. (b) In a cylindrical twist, equidistant helices are drawn on a series of coaxial cylinders, and the angle of the helices rotates regularly from one cylinder to the next. (b') Conventional representation of a cholesteric geometry applied to a cylindrical twist.

FIG. 14B depicts AFM measurement of collagen layer showing the preferred orientation and the uniaxial orientation (which is parallel to the coating direction). FIG. 14C depicts a typical height histogram of the collagen coating made according to the present invention, such as the one depicted in FIG. 14A. FIG. 14D depicts a density plot of 2D Fourier transformation of the function corresponding to the upper image at the FIG. 14A.

DETAILED DESCRIPTION OF THE INVENTION

Figure 1A:
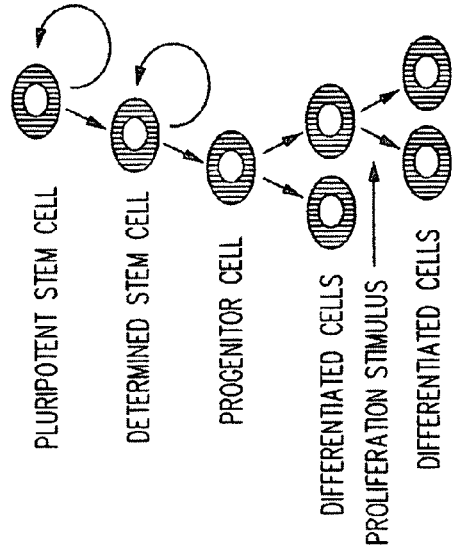
FIG. 1A shows a diagram depicting the known hierarchical design of collagen. The structural features of collagen range from the amino acid sequence, tropocollagen molecules, and collagen fibrils to collagen fibers.
Figure 1B:
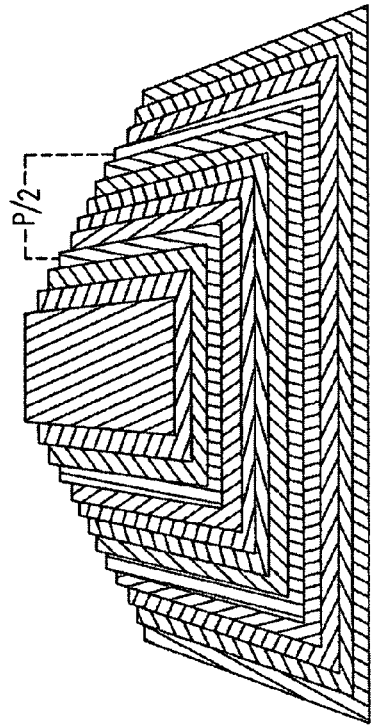
FIG. 1B depicts the transformation of stem cells.
Figure 2:
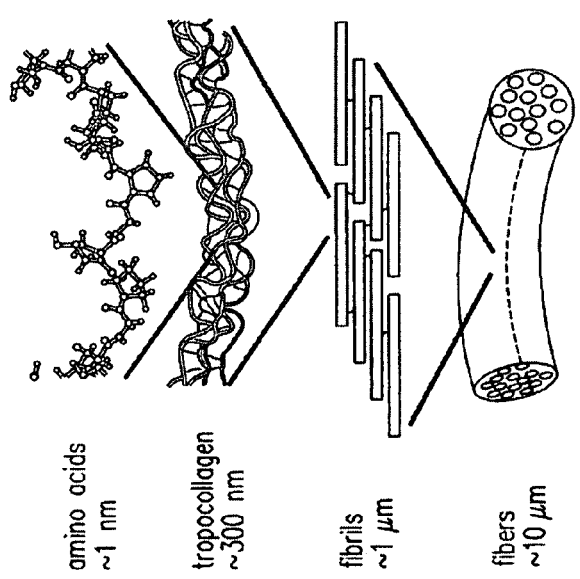
FIGS. 2A-2C are schematic drawings illustrating structures of liquid crystals in smectic, nematic and cholesteric form, respectively, made of rod-like structures such as molecules, microfibrils or fibrils reported in the prior art (A. C. Neville, BioEssays 3: 4-8 (1985)).
Figure 3:
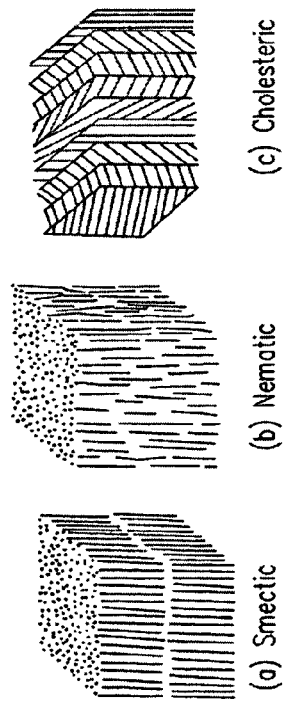
FIG. 3 is a diagram depicting the twisted plywood model as reported by M. M. Giraud-Guille, Int. Rev. Cytol. 166:59-101 (1996).

It is to be understood that both the foregoing general description and the following detailed description are exemplary and explanatory only and are not restrictive of the compositions, films and methods described herein. In this application, the use of the singular includes the plural unless specifically state otherwise. Also, the use of "or" means "and/or" unless state otherwise. Similarly, "comprise," "comprises," "comprising," "include," "includes" and "including" are not intended to be limiting. The terms "layer" or "film" or "thin film" or "matrix" may be used interchangeably throughout the description. The terms "uniaxial pattern" or "linear pattern" or "uniaxial collagen" may be used interchangeably throughout the description.

In general, embodiments of the present invention are related to collagen materials, compositions and films, and to methods of making and using the same. In some embodiments the present invention provides "linear pattern" or "uniaxial pattern" or "oriented pattern" collagen compositions and films, and methods of making. Without limitation, the term "linear" or "uniaxial" or "oriented" pattern collagen as used herein means collagen material or film that is a similar representation of the structure of collagen found in human or animal tendon tissue. In some embodiments, methods of generating one or more layers or films of collagen on a surface are provided wherein collagen is formed in a substantially uniform manner with a desired orientation on the surface of a substrate.

I. Collagen Compositions, Materials or Films

The present invention related to method of producing collagen coatings and films of a controllable thickness, a high degree of uniformity, a high degree of parallel orientation. Co-pending U.S. patent application Ser. No. 11/951,324 describes methods of making collagen material with woven pattern that resembles the collagen layer of the skin, the disclosure of which is incorporated herein by reference in its entirety. The present invention relates to the methods of making collagen material with uniaxial pattern that resemble the natural collagen matrix found in tissues such as but not limited to: tendon.

In one aspect, the present invention provides processes that produce collagen coatings and films of a controllable thickness, a high degree of uniformity, a high degree of parallel orientation.

In another aspect, the present invention provides a monolayer or a multilayer stack comprised of a collagen material, wherein at least the surface of said collagen material comprises a plurality of crimped fibrils with at least one preferred orientation, and the collagen layer has a uniaxial orientation.

Collagen proteins are comprised of polypeptide chains (a-chains) that form a unique triple-helical structure that is 300 nanometers long and 1.5 nanometers in diameter. Several of single collagen right-handed triple-helical molecules form a microfibril, which in turn aggregate to form fibrils. The fibril forming collagens, types I, II, III, V and XI, are the major structural proteins of skin, cartilage, bone, blood vessel walls and internal organs. King et al., Protein Engineering, 9:43-49, 1996. These types of collagens tend to self-assemble into periodic, cross-striated fibrils (or fibers), which can reach centimeters in length and tens of microns in diameter.

By "fibrils" or "collagen fibrils" herein is meant collagen molecules packed into an organized overlapping bundle. Collagen fibers are bundles of fibrils, however these terms are often referred to interchangeably due to different cross sectional diameters for the different types of collagen. For purposes of the present invention the terms fibril or fiber may be used interchangeably, but generally refer to collagen bundles having a cross sectional diameter in the range of about 30 nm to 2 microns.

Figure 5B:
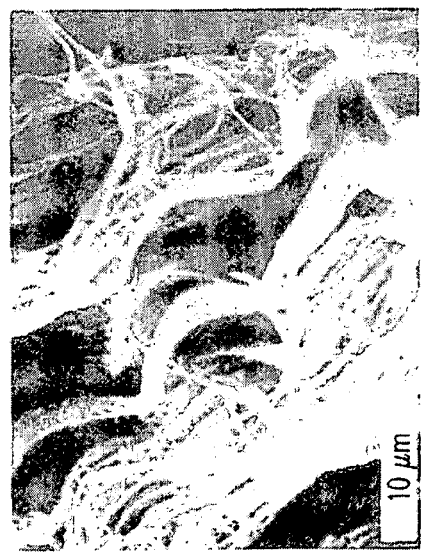
FIG. 5B depicts a helical-like fiber model of the collagen layer according to the present invention.
Figure 5A:
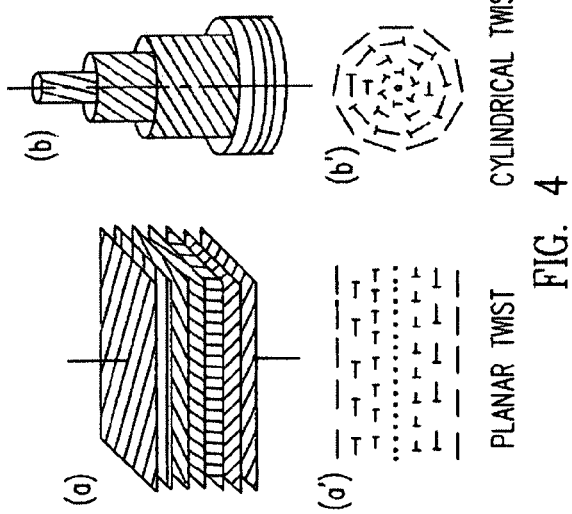
FIG. 5A is a SEM photograph showing the helical nature of crimped collagen fibrils in chordac tendineae taken from a porcine mitral valve.

By "crimped fibril", "crimped collagen fibril" or "corrugated fibril" herein is meant a two-dimensional (2D) or three-dimensional (3D) structure. These fibril structures may exhibit a variety of shapes and are not limited to any one shape. For example, the crimpled fibrils may be wavy or/and twisted. Usually the crimped fibril (or fiber) considered here is 3D structure but in some cases it can be a deformed two-dimensional (2D) structure (such as a sinusoid-like or serpentine-like structure). In some embodiments, the crimped fibril is a 3D helical-like fibril (for example, see FIG. 5A). In some embodiments, the helical-like fibril is a helical fibril, which has circular structure (for example see FIG. 5B). In some embodiments, the helical-like fibril resembles helices. In some embodiments, the helical-like fibril has a non-perfect circular structure. Generally, 3D structures formed by collagen fibrils that have small regular folds.

By "preferred orientation" or "preferential orientation" herein is meant that a similar orientation of biological or synthetic fibers or molecular chains in every part of the sample. For example, in some embodiments, the fibrils have a similar orientation in a collagen-based matrix.

Figure 6:
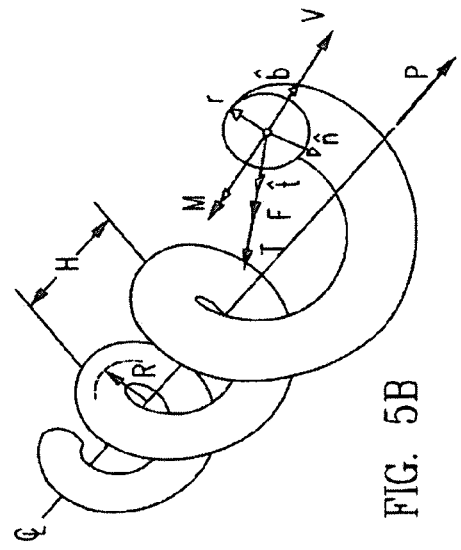
FIG. 6 depicts fibrils network (left) and its orientation distribution function (right).
Figure 4:
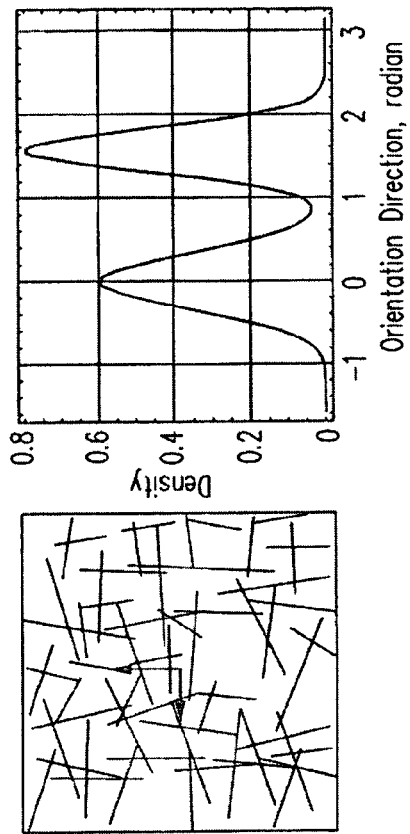

One of the main structural characteristics of the network or plurality of crimped fibrils is its orientation distribution function. An example of the orientation distribution function as used herein is presented at FIG. 6. We see here two preferable orientations at zero degree and 90°. Higher alignment is seeing at 90° direction. Thus, if one has a distribution function of different orientation and there are several peaks in this function then each peak represents a preferential orientation.

The collagen layer of the present invention also has a uniaxial orientation. By "uniaxial orientation" herein is meant orientation substantially parallel to the orientation of the coating direction of making the collagen layer, as described in more detail below.

If there is only one preferred orientation of a plurality of crimped fibrils then this orientation coincides with the uniaxial orientation and usually coincides with the coating direction.

Figure 7A:
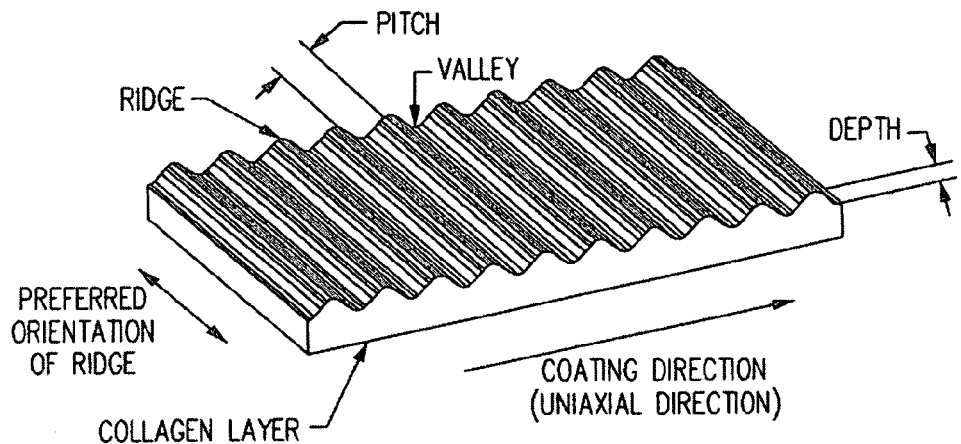
FIG. 7A is a schematic representation depicting one possible model of how the crimped collagen fibrils are formed collagen layer in some of the embodiments of the present invention.
Figure 8A:
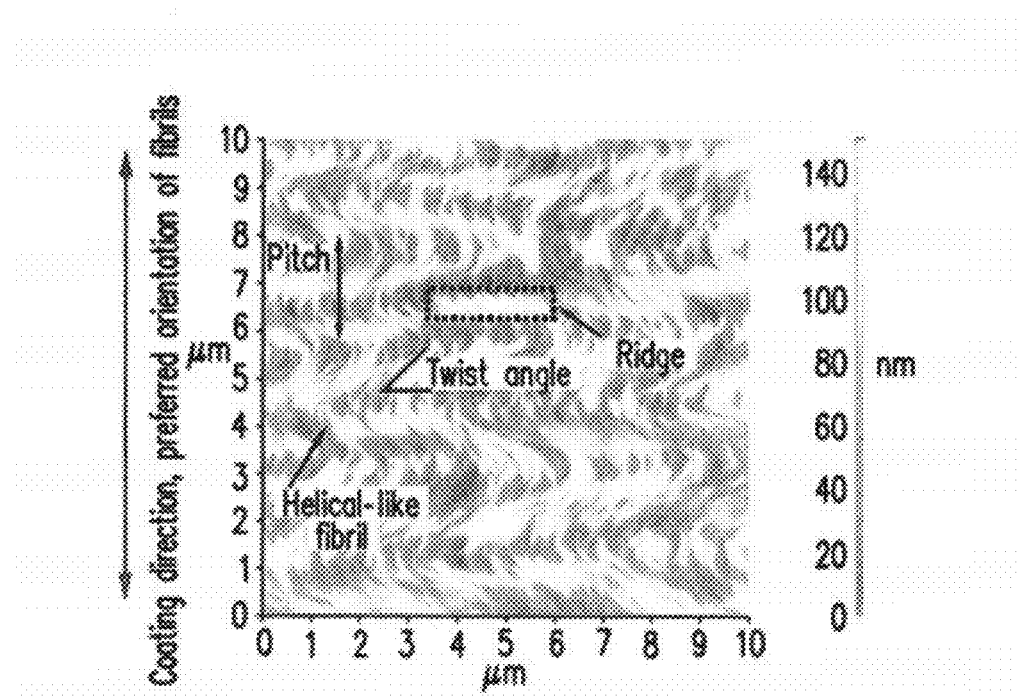
FIG. 8A is a AFM image of a bovine collagen layer formed according to embodiments of the present invention.

In some embodiments, the plurality of crimped fibrils form a crimped fibril assembly, and the assembly comprises a plurality of ridges and valleys, as shown for example in FIG. 7A. Thus, in this embodiment, the assembled crimped fibrils create a well-distinguished repeatable pattern with characteristic parameters. Generally, the pattern is comprised of an alternating series of ridges and valleys. As shown in FIG. 8A, the geometry of the pattern can be described by the pitch, twist angle, and the distance between the ridges, and is described in detail below.

In some embodiments, the crimped fibrils display at least partial translational order that correlates to the preferred orientation of the crimped fibrils. By "translational order" herein is meant an approximate invariance of the pattern with respect to discrete linear translation in some fixed direction (for example, in the direction of the ridge). By "orientational order" herein is meant some order of structural elements which have an orientational axes. By "alignment angle" herein is meant the angle between planar substrate and structural element having orientational axis (for example, crimped collagen fibril). See. P. G. de Gennes, The Physics of Liquid Crystal, Clarendon Press Oxford, 1974, herein is incorporated by reference. In other embodiments, the crimped fibrils do not display at least partial translational order but they still have the orientational order and the preferred orientation of the crimpled fibrils.

Figure 7B:
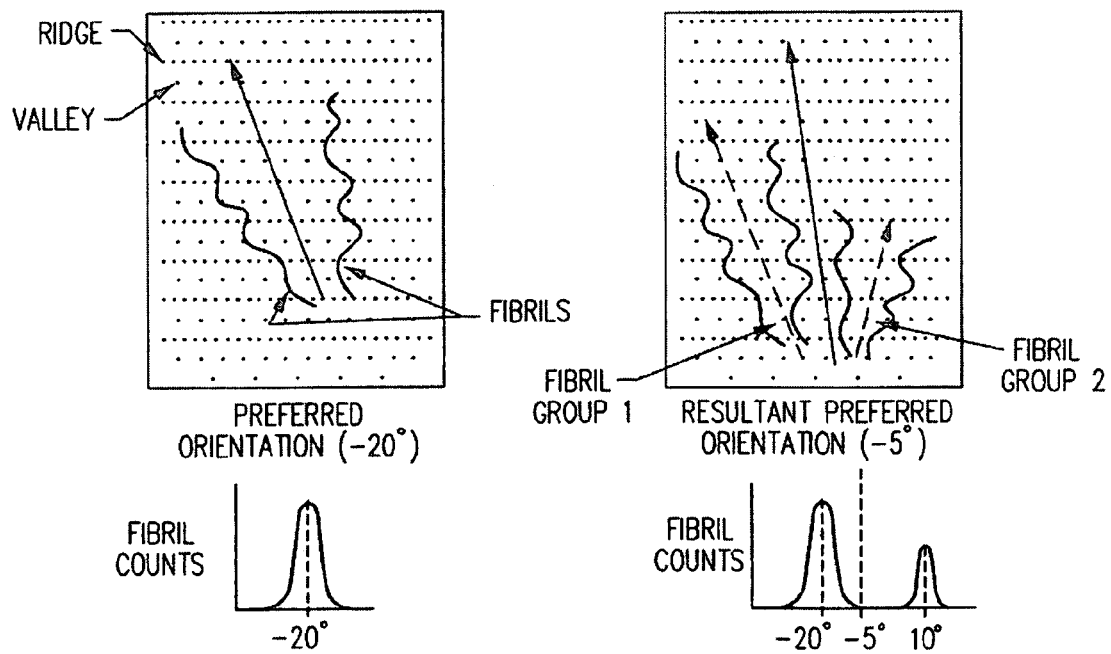
FIG. 7B depicts examples of preferred fibril orientation in some of the embodiments of the present invention. In the case of two fibril groups having their own localized preferred orientation, the resultant preferred orientation is also called the uniaxial orientation.

In some embodiments, the crimped fibrils are helical-like fibrils having upper and lower helixes and where the upper helixes of said helical-like fibers form said ridges and the lower helixes of said helical-like fibers form said valleys. This arrangement is shown for example in FIG. 7. As mentioned above "helical-like fibril" herein may include a helix-like fibril, which may either a 3D or 2D structure. Thus in some embodiments, the helical-like fibrils display a long-range orientational order. Long-range orientational order of biological or synthetic fibers (e.g. collagen fibrils) or molecular chains in the sample (e.g. a collagen-based matrix) means that at least one preferential orientation in the large area of the sample exists. In this case the preferential (or preferred) orientation is called director.

Bundles of crimped fibrils may display director orientation, which may vary within certain degrees throughout the matrix formed by collagen. Preferably, the direction orientation of the crimped fibrils is substantially parallel to each other. In some embodiments the alignment angle variation of said crimped fibrils is less than ±15°. The narrow range of angular director orientation variability is characteristic of the "linear" or "uniaxial" appearance of the matrix.

In some embodiments, there are at least 10 aligned crimped fibrils per 50 μm wide area of the collagen layer. Preferably 50 aligned crimped fibrils per 50 μm wide area of the collagen layer. Generally, the preferred number of aligned crimped fibrils per per 50 μm wide area of the collagen depends on the type of collagen. For example, rat-tail has much thinner fibrils then human or bovine collagen.

In some embodiments, the cross section of said fibrils is at least 30 nm, preferably 30 nm to 2000 nm, and more preferably 50 nm to 500 mm.

In some embodiments, the length of the fibrils is at least 2 μm, preferably 3 μm to 50 μm and more preferably 5 μm to 20 μm.

In some embodiments, the pitch of the helical-fibril is at least 100 nm, preferably 100 nm to 2000 nm, and more preferably 100 nm to 500 nm.

In some embodiments, the valley is about 10 to 1000 nm deep, preferably 20 nm to 500 nm, and more preferably 50 nm to 100 nm.

Figure 8B:
FIG. 8B depicts a tendon tissue micrograph. The scale bar=0.1 mm. All the gray area is collagen, aligned parallel to the applied muscle force. Small dark features are nuclei of fibroblasts distributed throughout the structure. Large dark regions are blood vessels, which enter only from ends.

Generally, the uniaxial pattern formed on the surface of the collagen layer is detected by AFM (Atomic Force Microscope), as shown in FIG. 8B. In one embodiment, the basic elemental pattern is formed by two adjacent ridges and the valley in between. There may be more than one elemental pattern, each of which may have a different direction of alignment. The average distance between two nearest ridges or valleys defines the pitch of the structure. Fibrils in the two nearest ridges have opposite directions. The important result of Atomic Force Microscope measurement is the surface topography of the surface of the collage layer. One example of this measurement is shown in FIG. 9B which is an AFM measurement of a rat-tail collagen coating on a glass substrate according to one embodiment of the present invention. The preferred orientation of the crimped fibrils is shown by yellow arrow, and blue arrows show the preferred directions of the "ridge formations".

The collagen layer pattern can be further characterized by the average length and width of the ridges and valleys. The particular patterns are strongly dependent on collagen material and coating conditions. The length of the pattern is normally much larger than the pitch and varies from hundreds of nanometers to tens of microns. The width of ridges and valleys is generally in the range of 100 nm-100 microns. Commonly, the width of the ridges and valley are not equal. The width of the ridges in some collagen films is larger than the width of the valleys. The reverse can also be so for different collagen material or coating conditions. The depth of the structure is measured as the distance between the top of ridge and bottom of the valley and generally varies in the range of 10 nm-1000 nm.

The preferred alignment of the pattern can be defined as the mean orientation of ridges or/and valleys. It is tightly correlated with the preferred direction of the fibrils and has two principal types of alignment. In the first type of alignment, the pattern is aligned in a direction perpendicular to the mean direction of fibrils. In the second type, the pattern has two preferred directions relative to the mean direction of fibrils. The angle between these two preferred directions can vary in the range of about 40-180 degrees.

The structure characteristics of the collagen layer provided by the present invention can be determined by a variety of methods known in the art. For example, the structure characteristics of the collagen layer can be determined by the diffraction pattern when illuminated by a light source, such as a collimated monochromatic light source having a visible wavelength.

Figure 9A:
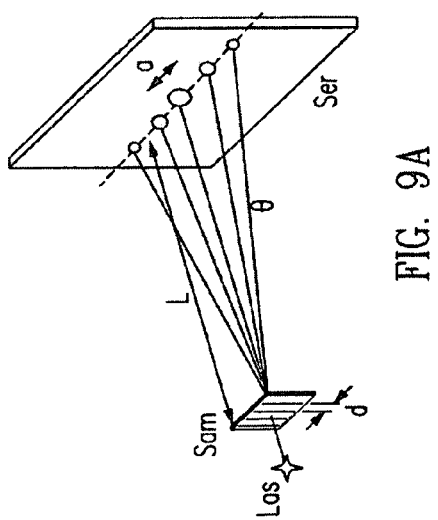
FIG. 9A depicts the diffraction measurement setup used to detect diffraction patterns from collagen layers of the present invention. Las: Laser beam; Sam: sample; Scr: screen.
Figure 9B:
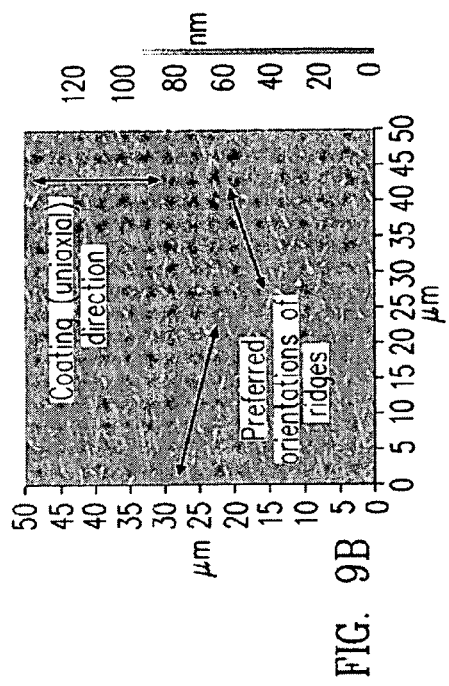
FIG. 9B depicts the topography of the surface of the rat-tail collagen I coating.

In one aspect of the invention, the diffraction pattern of the collagen layer is measured by a Fourier image setup as depicted in FIG. 9A. In this setup a collimated monochromatic light source with visible wavelength is positioned before a sample (in this instance a collagen layer according, to the present invention) and a diffraction pattern is produced on a screen. The presence of two symmetric petals in diffraction pattern provides strong evidence of the linear orientation of fibrils, or ridges, or some other structural elements in the volume of the sample. The distance between petals has a strong correlation with the average distance between fibrils in the parallel alignment or between ridges. Combination of AFM measurements and diffraction measurements reveal the fine structure of the developed materials.

Figure 9C:
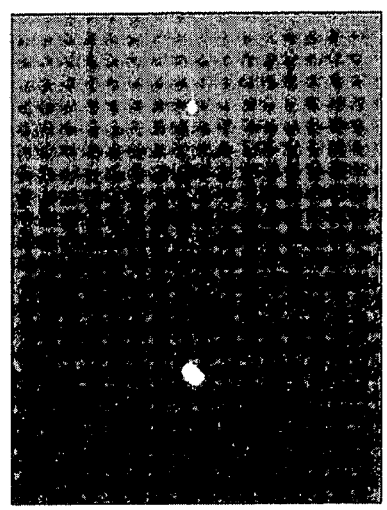
FIG. 9C depicts the diffraction pattern of the rat-tail collagen coating as shown in FIG. 9B.
Figure 9D:
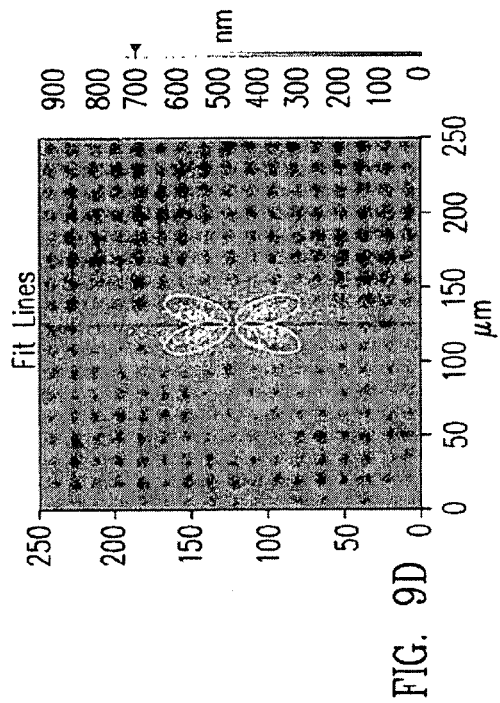
FIG. 9D is a photograph depicting the diffraction patterns of the collagen layer as shown in FIG. 9B.

One example of the fast Fourier transformation (Fourier image) of the surface topography as shown in FIG. 9B is presented at the FIG. 9C. One can see four highlighted petals, which correspond to the partial translational orders. The same sample transmitted by collimated laser beam with wavelength 650 nm has diffraction pattern shown at the FIG. 9D. This pattern represents a bulk orientational order of the collagen coating.

Figure 10A:
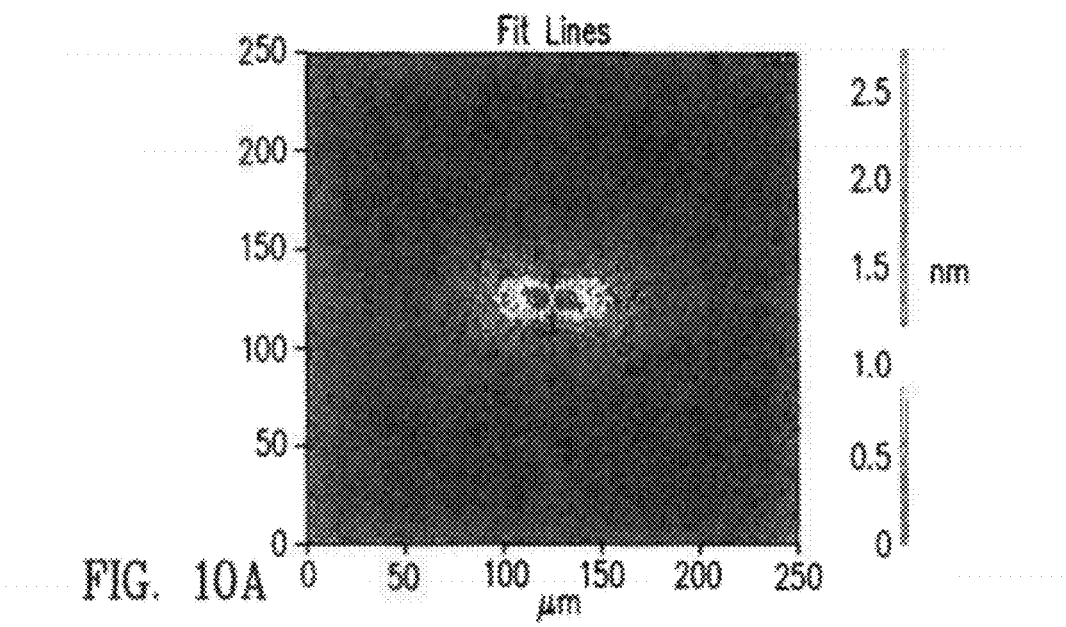
FIG. 10 A-B are photographs depicting the diffraction patterns of the collagen layer in some of the embodiments.
Figure 10B:
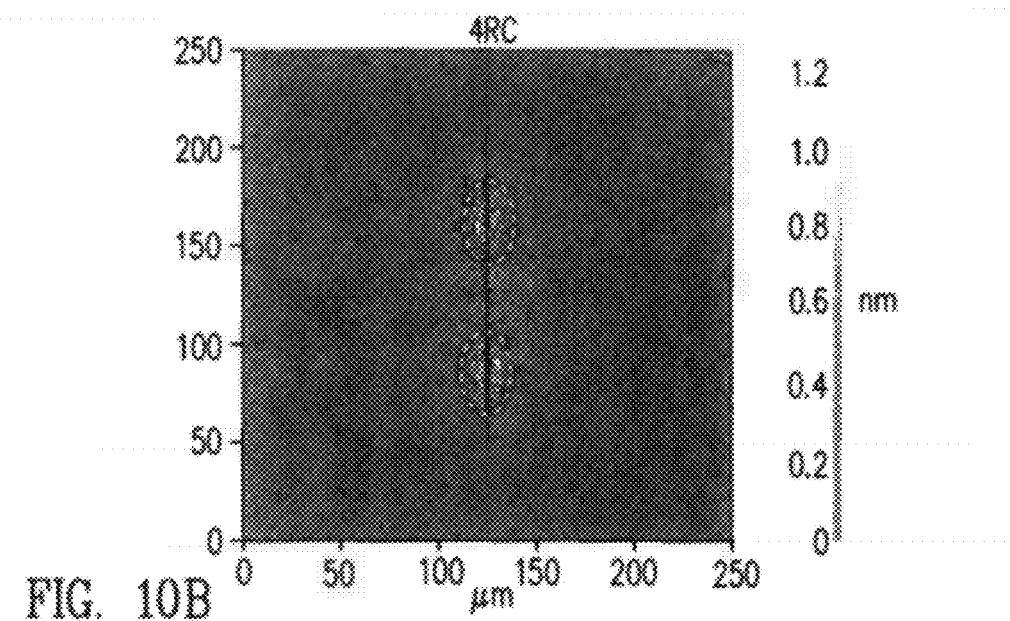

In some embodiments, the topography of the surface of the collagen layer has anisotropic Fourier image containing at least two pedals, as shown in FIG. 9C and FIGS. 10A and 10B.

In some embodiments, the collagen layer produces an anisotropic transmission diffraction pattern containing at least two petals when exposed to a collimated monochromatic light source having visible wavelength.

In some embodiments, the collagen layer produces anisotropic reflective diffraction pattern containing at least two petals when exposed to a collimated monochromatic light source having visible wavelength. Herein the reflective configuration of the measurement setup is used instead of transmission one.

Figure 11B:
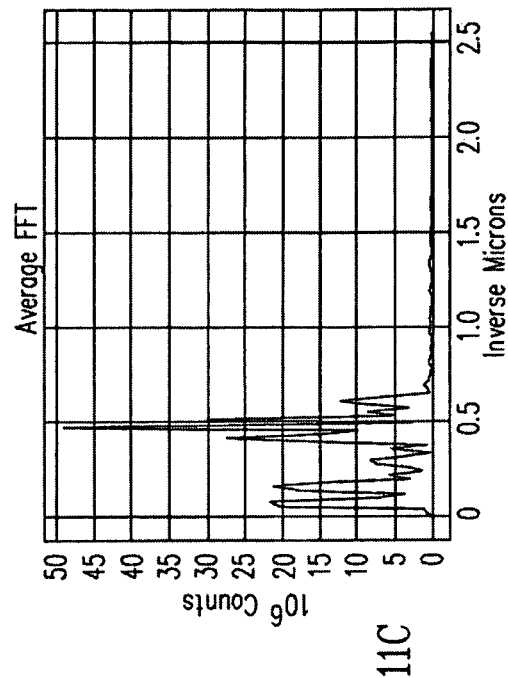
FIG. 11B depicts the fast Fourier transformation (FFT) X-axis. The X-axis is in inverse microns. The peak is at the 0.5 inverse micron, which indicates the pitch of 2 μm.
Figure 11C:
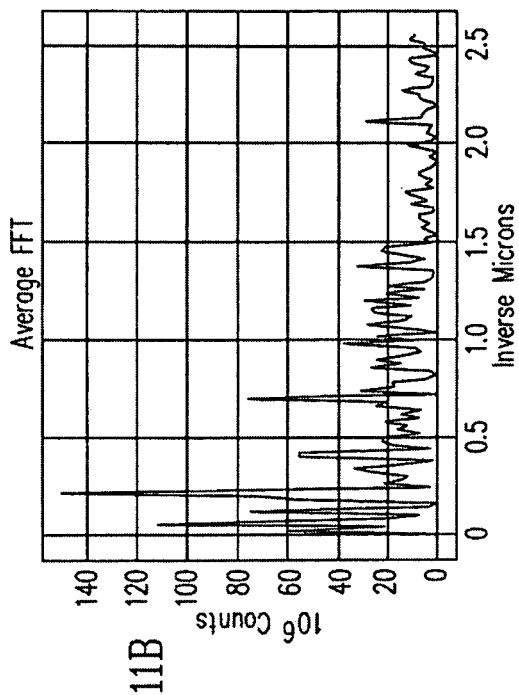
FIG. 11C depicts the digital FFT Y-axis. The Y-axis is in inverse microns. The FFT images show the surface topography (1D Fourier image) of the collagen layer, and shows anisotropy and some details of the surface structure.
Figure 11A:
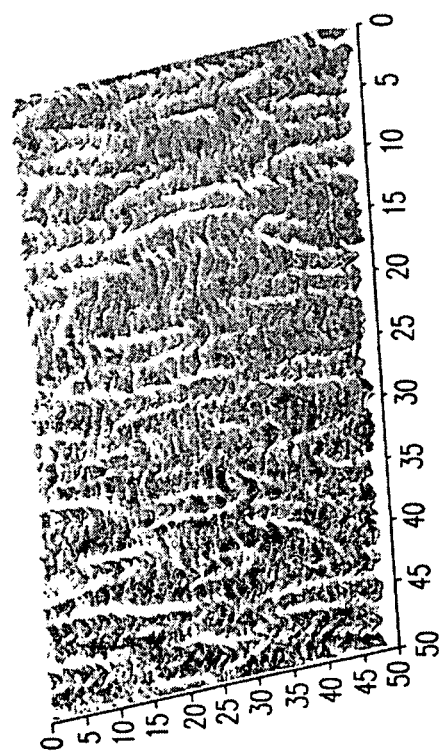
FIG. 11A depicts the AFM images of bovine collagen type I (50 λm×50 μm). The ridges have a pitch (distance between adjacent ridges) of 2 μm.

The uniaxial pattern observed under the AFM is consistent with the periodicity observed as Fourier transformation. FIG. 11 shows the AFM images of collagen layer made of bovine collagen and the Fourier transformation of the same sample. The periodicity in the X and Y direction of the collagen layer is revealed by the peak in the X and Y direction of the Fourier transformation.

Figure 12:
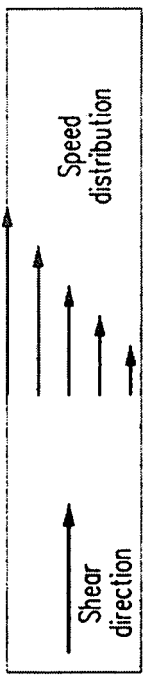
FIG. 12 is a schematic representation showing how the shear direction is defined, according to some embodiments of the present invention.

In some embodiments, the ridges of the upper helixes of the helical-like fibrils form a angle of at least 30 degree with the preferred orientation. For example, as shown in FIG. 8A, the helical-like fibrils have a preferred orientation that is perpendicular to the shear direction. By "shear direction" here in is meant the direction that is perpendicular to the gradient of the speed distribution of the liquid layer. See FIG. 12. In some embodiments, the shear direction of each layer may not necessarily be parallel to each another. The twist angel is more than 30 degrees as indicated in the drawing.

In some embodiments, the monolayer or multilayer stack comprises at least two collagen layers, wherein said uniaxial direction of each collagen layer may not necessarily be parallel to each another.

In some embodiments, collagen materials of the present invention are modified by incorporating hydrogels, peptide based biomaterials, and other bioactive materials, including but are not limited to, incorporated ligands, encapsulated DNA, and growth factors into the collagen material matrix. For example, proteins such as fibronectin promote, cell attachment to collagen. Various synthetic peptides comprising biologically active amino acid sequences can be covalently attached to obtain a desired biological activity. Various proteoglycans will bind tightly to collagen, bind a variety of growth factors and enhance desired biological activities including tissue repair and regeneration.

In another aspect, the collagen-based material provided herein further comprise nanorods, nanowires (for example, carbon nanotubes or silver/gold nanowires), and other additives (for example, sulfonic liquid crystals) to enhance optical and electromagnetic characteristics of the collagen material. Many of these additives can preserve the liquid crystal state of the collagen coating material. A magnetically-guided microfabrication system was recently introduced in R. Valluzzi et al., Philosophical Magazine, 84:3439-3447 (2004), and may be used to attach artificial magnetic particles to the collagen materials of the present invention molecules.

Of particular advantage, the collagen materials provided by the present invention may further form membranes, films, and mono- or multi-layers comprised of linear pattern collagen material. For example in some embodiments, the collagen material comprises a monolayer or multilayer stack comprises at least one collagen layer as provided herein.

In some embodiments, the multilayer structure may have different functional layers including a collagen layer. The property of the first layer on the substrate can be chosen to enable easy delamination of the whole structure. By "functional layer" herein is meant a layer that has an important function (for example, biological or mechanical function) in the layer application. Thus a functional layer serves functional, as oppose to, or in additional to, structural purpose. For example, the functional purpose can be providing a surface for cell adhesion or ligand coupling. In some embodiments, the functional layer includes, but is not limited to: lipid membrane, coagulant, living tissue cell layer, adhesion promotion layer, carrier layer, protective layer, delaminating promotion layer, and combinations thereof.

In some embodiments, an additional cross-link is applied to the collagen-based matrix to increase its stability and mechanical strength (especially in the cross-orientational direction). Several types of cross-links can be used for collagen fibrils. Included are UV treatment, intra-monomeric disulfide bridges, glycosydic cross-links formed via nonenzymatic glycation, Howard et al.; Experimental Cell Research, 228:132-137 (1996), interstitial phosphate and sulfate cross-links, Mertz and Leikin, Biochemistry, 43:14901-14912 (2004), and covalent linkages promoted by the activity of the enzyme lysyl oxidase, Siegel, International Review of Connective Tissue Research, 8:73-118 (1979).

II. Method of Making

Methods of making collagen matrices, and in particular uniaxial pattern collagen matrices and films are provided. Of particular development, in some embodiments collagen material is produced using a collagen starting material in liquid crystal form.

In some embodiments, a concentrated liquid collagen solution (usually acid molecular solution of collagen) is used to prepare the collagen-based layer. It can have some additives such as ATP to decrease the threshold of the required concentration to develop the liquid crystal state. Without being bound by any particular theory, generally, highly negative charged molecules (more that −3) can be used as additives to the collagen solution to promote the orientation or adhesion of the collagen, so that the collagen can form liquid crystals at relative lower concentration. Suitable additives include, but are not limited to ATP, vanadate, insulin, phosphate and VGF.

The coating process generally starts with a water based acidic solution with molecular collagen. Each collagen molecule is about 300 nm long and 1.5 nm wide. The solution is then concentrated. At certain concentration (the actual concentration depends on the collagen type being used) the solution forms a liquid crystal. This liquid crystal used as coating material. Coating is conducted by applying a shear force to the collagen solution which aligns the collagen in the coating direction. After the coating is formed, the coating is dried and the molecular collagen self-assembles into helical-like fibrils.

Collagen films can be made by coating collagen on to methacrylate or other surfaces including glass, other plastics, metals, semiconductors, or biological materials. This technique is useful in preparing collagen in a variety of ways for both physical and biological testing, and this type of study should lay the foundation for utilizing collagen as a biomaterial. For example, the ability of a collagen substrate in vitro to support cell attachment, migration and survival, may help in predicting its activities when implanted in vivo.

Embodiments of the macroscopically oriented collagen film pursuant to aspects of the present invention may be created from a liquid solution of collagen which is comprised of rod-like structures such as molecules, microfibrils or fibrils. In some embodiments, before the collagen can be successfully coated, a nematic liquid crystal form of this solution must first be created by changing characteristics of commercially available concentrations of collagen to concentrations of about 10 mg/ml-30 mg/ml, pH of about 2-6, and temperature conditions of about 4-25° C. and possibly including additives, etc. In some embodiments, type I collagen or other forms of molecular collagen can be used, and the collagen can be from human, rat, bovine, or other source. The collagen can be obtained either by extracting from a natural source, or generated by genetic engineering. In some embodiments type I bovine collagen is used.

In an illustrative example, collagen-starting material is provided comprising a monomeric human or bovine collagen I in an acid solution, for example without limitation an acetic acid solution, wherein the nematic collagen is present at a concentration of (10 mg/ml to 30 mg/ml). Embodiments of the present invention provides for nematic and cholesteric phases of the human Collagen I by self-assembly of the monomeric collagen in acidic solution at certain concentration and temperature (e.g., 10 mg/ml and 6° C.). Of particular advantage the inventive methods and compositions promote maintaining and preserving the native liquid crystal structure of collagen-like materials.

In some embodiments, the liquid crystal state of the collagen is selectively controlled. Selective control can be achieved by a variety of methods, including but not limited to: observation of typical pattern in the material between crossed polarizes with and without staining or/and retardation enhancement; polarized microscopy with and without staining or/and retardation enhancement; Mueller matrix measurements, and polarimetry (i.e., Axometrics polarimeter). It has been shown that high concentrations (5-30 mg/ml, depending on the collagen type) of procollagen molecules in physiological buffer develop long range nematic and precholesteric liquid crystal ordering extending over 100 µm$^2$ domains, while remaining in solution (R. Martin et al., J. Mol. Biol. 301: 11-17 (2000)). Procollagen concentrations in vivo are estimated at several tens of milligrams per milliliter in the secretory vesicles and the molecules are often observed to be aligned in a nematic-like ordering.

In some embodiments, the collagen is concentrated by various methods known in the art, including but is not limited to filtration, rotary evaporation, and dialysis membrane.

In another embodiment, the collagen material may be prepared by ultrasonic treatment. Brown E. M. et al. Journal of American Leather Chemists Association, 101:274-283 (2006), herein is incorporated by reference by its entirety.

There are numerous ways to achieve such deposits depending on the surface to be coated, the area to be coated and the homogeneity desired.

Collagen layers provided herein may be produced by slot die technology. In one example, slot die technology as described in Chang Y R et al., Journal of Colloid and Interface Science 308:222-230 (2007), Paukshto M., et al., Journal of the SID 13:765-772 (2005); Fenell, L., et al., Asian Display/IDW '01:60'-603, and U.S. Pat. Nos. 4,299,789, 4,869,200 and 6,174,394, all expressly incorporated by reference in their entireties, may be employed.

Of particular advantage, in one embodiment collagen layers are produced by application of a shearing force. This inventive method allows for specific arrangement of the collagen fibrils and promotes the formation of selective patterns in the resultant collagen matrices and films. The inventive method may be used to maintain and preserve the native phase of the collagen-based materials. In an illustrative embodiment, methods of forming at least one collagen layer are provided comprising the step of applying a shear force to a collagen solution at a shear rate of about 5 to 100 mm per second, preferably 10 to 1000 mm per second.

In some embodiments, the collagen starting solution is present in a liquid crystal state. In another embodiment, the collagen solution is present in a nematic liquid crystal state at a concentration of 10 to 30 mg/ml, preferably 25 mg/ml to 30 mg/ml.

The shear force may be applied to the collagen solution by any suitable means. In one non-limiting example, the shear force is applied using a slot die tool, operated under pressure. The collagen solution may adjusted for concentration, pH, temperature, salt constituents and other factors and before being forced through the slot die under pressure onto a clean desired surface, such of glass, plastic or other substrate material. The application process may be computer controlled to assure homogeneity of coating, depth of deposit and other desired parameters.

In another non-limiting example, the shear force is applied using a liquid film applicator assembly as described in International Patent Application Serial No. PCT/US2007/024238, the entire disclosure of which is hereby incorporated by reference.

In another non-limiting example, the shear force is applied using two substantially parallel plates of suitably smooth material such as glass. The collagen material is deposited on the first plate. The second plate is placed on top of the first plate creating a "sandwich". A suitable force is applied to squeeze the two plates together to create a small gap between them. The first plate is translated relative to the second plate to create the shear force on the entrapped collagen material. The plates may be flat or planar. Alternatively, the plates may be curved have some other non-planar topography.

A variety of parameters have been found to influence the orientation of the collagen fibrils. Some main method parameters which influence the collagen orientation, are: shearing force speed, coating gap, shearing plate smoothness, shearing plate surface energy, collagen concentration and additives, relative humidity and temperature, drying speed, and surface pretreatment.

In some embodiments, the method provided herein is used for the fabrication of a multilayer structure by sequential coatings. This multilayer structure may have different functional layers including a collagen layer. The property of the first layer on the substrate can be chosen to enable easy delamination of the whole structure.

In yet additional embodiments, linear pattern collagen materials and layers are formed by non-contact slot-die type methods according to the present invention. In this embodiment, methods are characterized by any one of more of: (1) high shearing speed; (2) high fluid material consumption of a starting collagen solution in order to fill the die cavity and pump with collagen solution; (3) controlled gap distance; (4) long length of shearing zone; and/or (5) in-situ control of alignment and drying.

Figure 13:
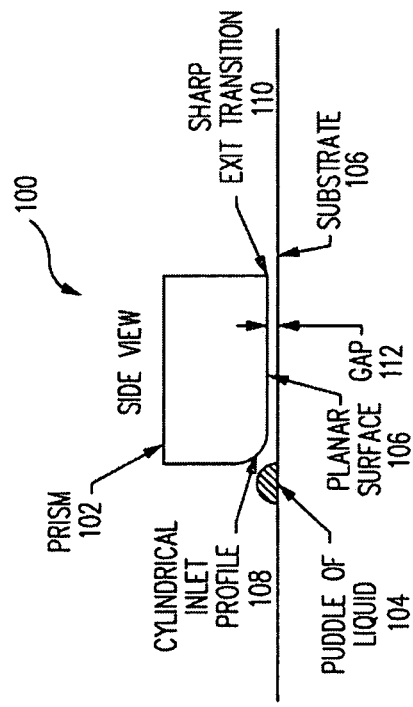
FIG. 13 depicts a slot-die type coating system, which may be used to carry out methods of the instant invention.

Included as aspects of embodiments of the present invention are methods of creating a collagen fibril, and the key properties of a unique type of macroscopically oriented collagen film. In certain embodiments of the present invention, this film can be prepared by subjecting a nematic liquid crystal collagen solution to adequate shearing forces. The method of applying these shearing forces can be done, for example, using the novel and inventive (slot-die type) coating system as shown in FIG. 13, and is described in more detail in International Application Serial No. PCT/US2007/024238, the entire disclosure of which is hereby incorporated by reference. This system has very low fluid material consumption, precisely controlled coating gap, and long length of shearing zone. The inventive system enables the production of the macroscopically oriented collagen film shown in FIG. 14A, which illustrates an embodiment of a material, composition of matter and/or product according to aspects of the present invention.

In one example, a system which may be used to carry out the method is shown in FIG. 13. The coating system 100 may comprise a prism 102 made of a hard material, such as stainless steel and the like. The prism 102 is precisely positioned over a smooth substrate 104, (such as glass, to form a gap 112. Components of the prism 102, in some embodiments, include an inlet profile 108, in some embodiments typically of cylindrical shape, a planar surface 106 polished to a high degree of flatness blended smoothly with the inlet profile and a sharp edge 110 which forms the transition at the exit of the gap 112. The method of positioning the prism over the substrate to form a precise gap is not discussed here. In some embodiments, a narrow strip of collagen solution liquid is deposited on the substrate to form a puddle 114. In certain embodiments, the liquid may be of sufficiently high viscosity to form a free-standing puddle. In some embodiments, the prism is held fixed and the substrate moves from left to right dragging the liquid into the inlet profile zone, causing the liquid to fill the gap until it reaches the exit. The gap can be in the range of 5-50 microns and the coating speed can range from 10 to 100 mm/sec. While in the narrow gap, the liquid is subjected to high shearing forces of sufficient time duration to cause it to become oriented. The sharp edge at the exit serves to minimize the size of the naturally occurring meniscus, which, if too large, would cause unacceptable streaking on the finished film. In alternate embodiments, the prism can be moved in relation to the substrate.

Figure 14A:
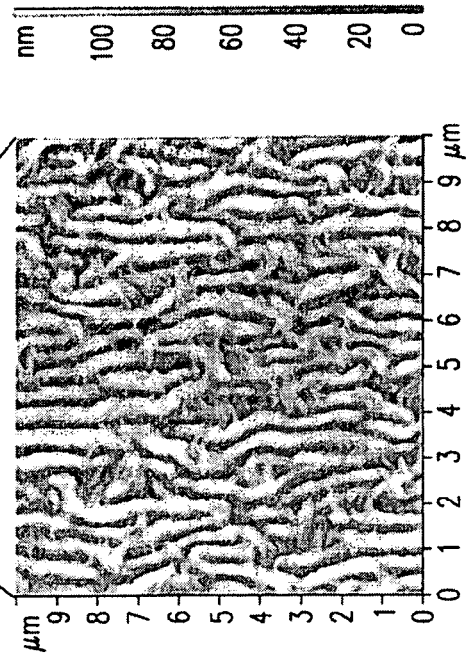
FIG. 14A illustrates an AFM image of a collagen film on glass made according to some embodiments of the present invention.
Figure 14A:
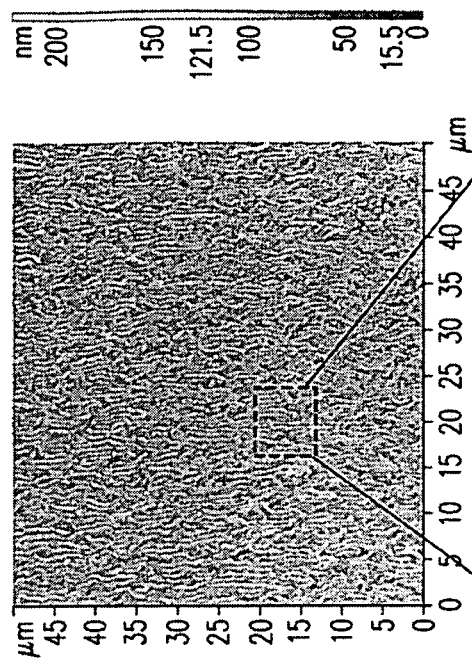

In the example to produce the product shown in FIG. 14A, a 10 mg/ml concentration of type I collagen was used, the prism was set at a 10 micron gap over the substrate, the prism was approximately one inch in width and made of stainless steel. The lower planar surface of the prism was manufactured to have a surface flatness of $\lambda/4$ ($\lambda=633$ nanometers) (peak to valley) (max). The surface of the one-quarter cylindrical inlet profile was manufactured to have a surface finish characteristic of commercial polish without blemish.

Without limitation in some embodiments, the shearing is speed is in the range of 10 to 100 mm per sec, more typically in the range of 20 to 60 mm per see, and up to 1000 mm per sec. The fluid material consumption is in the range of 0.5 cc to 2 liters, more typically 0.5 cc to 2 cc. The gap distance is generally in the range of 1 to 50 µm, and more typically in the range of 5 µm to 100 µm. The shearing zone has a length generally in the range of up to 30 mm, more typically in the range of 1 mm to 10 mm.

In some embodiments, the alignment and drying during coating process are controlled by a surface rubbing and air knife using nitrogen at the temperature in the range of 4° C. to 37° C., more typically 15° C. to 25° C.

Figure 15B:
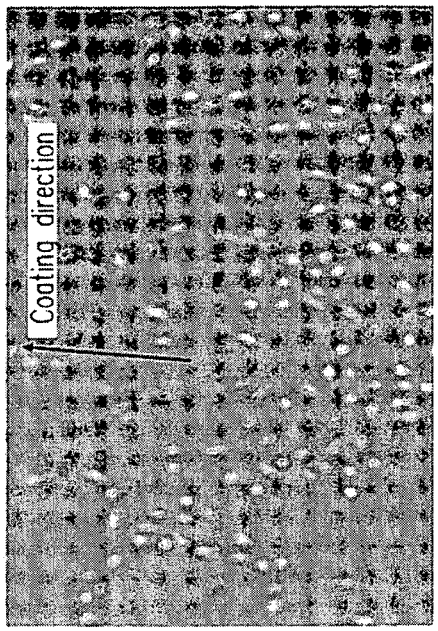
FIG. 15B shows the epithelial cells alignment on the oriented bovine collagen.
Figure 15A:
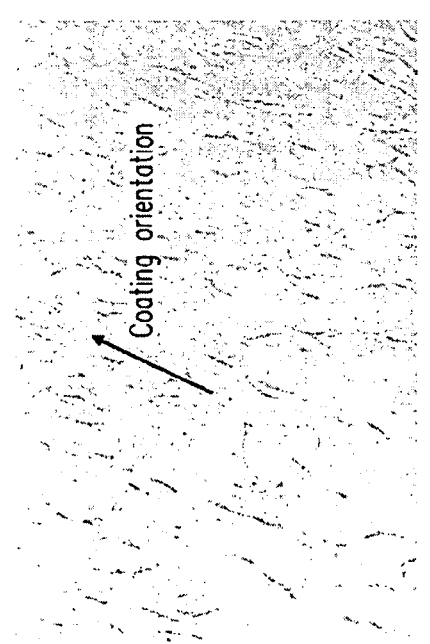
FIG. 15A shows human fibroblasts alignment on the oriented rat-tail collagen. The coating direction is indicated by the arrow.
Figure 15C:
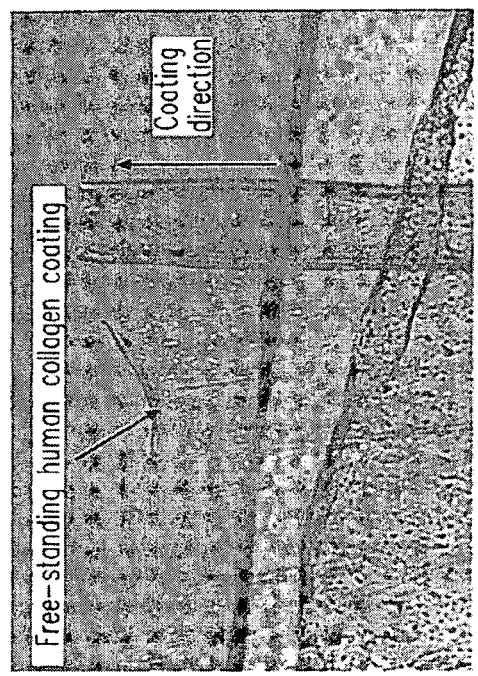
FIG. 15C shows endothelia cells alignment on the oriented human collagen. Free standing, delaminated sample of human collagen coating is shown at the FIG. 15C.

Then the sample was measured by AFM and the results are shown at FIGS. 8A, 9B and 15A.

Of particular advantage, this coating method of the invention presents the opportunity for multilayer roll-to-roll coating of biological materials on flexible substrates. This provides the opportunity for large volume production of biological materials on a scale not before enable, due in part because this embodiment of the method is a non-contact coating method, providing high alignment to lyotropic liquid crystals with very low fluid material consumption; and capable of a high level of uniformity.

If the profile of the coated collagen sample is measured within a representative area (for example 10 µm*10 µm) then a mean level of this profile can be always defined to be equal zero. Now one can obtain the height distribution function, J. M. Bennett and L. Mattson, Introduction to Surface Roughness and Scattering, OSA, Washington, D.C., 1999, 130p, (also called an amplitude density function).

Collagen based samples coated by methods of the present invention have non-symmetrical height distribution function of the surface profile. This type distribution was compared with normal distribution. The normal distribution has the same mean value (which is zero) and same rms value (see, for example, J. M. Bennett and L. Mattson, Introduction to Surface Roughness and Scattering, OSA, Washington, D.C., 1999, 130p,).

In some embodiments, the collagen layer provided herein can be produced by combining different deposition methods, such as by combining slot-die and then jet printing and patterning.

III. Applications

Solubilized, purified and reconstituted into oriented collagen materials and fibers of the present invention find use in many applications.

Films and matrices prepared from collagen materials according to embodiments of the present invention are among some of the most interesting materials from both practical and basic research aspects. In one aspect of the present invention biomedical devices are formed from the inventive collagen materials, films and matrices. Additionally, the surface of the collagen materials of the present invention can be studied in a wide variety of ways and modified for particular desired applications.

Collagen membranes for hemodialysis have been prepared by extrusion of a mixture of atelocollagen and dissociated, washed collagen fiber.

All collagen films and membranes age when dried and stored. Drying collapses and condenses the structure, and crosslinks appear over time. Aging can be prevented or slowed by keeping the collagen materials or membranes cold, in the dark, or hydrated.

In another aspect, the collagen-based matrices provided herein further can be deposited on the substrate that creates a pre-tilt angle of the collagen aggregates at the interface. It can be done, for example, by chemical or physical treatment of the substrate before coating. This process is similar to a forming of pre-tilt angles in liquid crystal display applications.

A. Cell Culture

In one aspect, the present invention provides linear pattern collagen materials and films that find uses in cell cultures.

Collagen as a film or as a coating on other materials has also been used in tissue culture for the growth of fastidious cells. The protein surface and the orientation of the fibers appear to promote cell growth in vitro and probably in vivo as well.

By "cell culture" or "culture" herein is meant the maintenance of cells in an artificial, e.g., an in vitro environment. It is to be understood, however, that the term "cell culture" is a generic term and may be used to encompass the cultivation not only of individual prokaryotic (e.g., bacterial) or eukaryotic (e.g., animal, plant and fungal) cells, but also of tissues, organs, organ systems or whole organisms, for which the terms "tissue culture," "organ culture," "organ system culture" or "organotypic culture" may occasionally be used interchangeably with the term "cell culture."

By "cultivation" herein is meant to the maintenance of cells in an artificial environment under conditions favoring their proliferation, differentiation, production of specific proteins both recombinant and natural or continued viability, in an active or quiescent state. Thus, "cultivation" may be used interchangeably with "cell culture" or any of its synonyms described above.

Generally, cell culture is carried out by growing cells in a culture vessel in the presence of cell culture medium. By "culture vessel" herein is meant a glass, plastic, or metal container and the like that can provide an aseptic environment for culturing cells. Culture vessels include but are not limited to petri dishes and 96-well plates.

In some embodiments, the linear collagen layer is used to coat the surface of a cell culture vessel.

The use of various biological macromolecules as coating has been widely employed in tissue culture as have their use in coating medical devices. Such biological materials include collagen, gelatin, fibronectin, fibrin, heparin and other factors. When used as coatings, these factors support better biocompatibility and include in the case of tissue culture to enhance the attachment, survival, growth, migration and differentiation of cells added to the dish. Current concepts suggest that, such coatings bind to receptors on the surface of the cells which then support the attachment multiplication and behavior of the cells. Such surfaces prepared using current methods are not necessarily homogeneous in terms of completeness of the coating. Moreover the structure that collagen, for example, which assumes on the dish generally in no way corresponds to the arrangement of collagen in the native tissues but is largely random.

The surfaces on which cells grow play a key role in controlling cellular behavior. Spradling A., et al., Nature; 414: 98-104 (2001); Streuli C. Curr Opin Cell Biol; 11(5): 634-40 (1999). Properties such as surface roughness, hydrophobicity, and specific interaction with the cell surface can all affect cell activity. Saltzman W M. Cell Interactions with Polymers. In: Lanza R P, Langer R S, Vacanti J, and editors. Principles of Tissue Engineering. 2nd ed. San Diego: Academic Press; 221-35 (2000). The modulation of cell activity through substrate interaction can have a significant effect on biomaterial-based therapies. Tissue engineered constructs, ex vivo cell propagation, and cell encapsulation all require some type of interaction between cells and supporting material for growth, function, and/or delivery. Lanza R P, Langer R S, Vacanti J. Principles of Tissue Engineering, 2nd ed. San Diego: Academic Press; 2000. The modulation of bioactivity through the rational design of materials has been widely investigated. Hubbell J A., Curr Opin Biotechnol 1999; 10(2): 123-9. One example includes hydrogels that can enhance cellular growth through incorporation of tethered adhesive ligands. Lutolf M P., et al., Nat Biotechnol 21:513-8 (2003). Material-based control of cellular function is a potentially powerful tool for controlling stem cells, which have the potential to differentiate into many tissue types. For example, a self-assembling peptide based biomaterial that can specifically direct the differentiation of neural progenitor into neurons was recently described by Silva G A., et al., Science 303:1352-5 (2004). Much research is currently focused on the development of bioactive materials through the incorporation of ligands, and encapsulation of DNA and growth factors Chen RR and Mooney DJ. Pharmaceutical Research 20:1103-12 (2003); Sakiyama-Elbert SE and Hubbell JA. Ann Rev Mater Res; 31:183-201 (2001).

In one aspect, the present invention provides a three-dimensional matrix for use in three-dimensional cell culture. The matrix comprises a collagen layer, said collagen layer comprising a plurality of helical-like fibrils with a preferred orientation over said surface, and wherein said helical-like fibrils display a long-range orientational order.

In some embodiments, the collagen layer is prepared by shearing and drying on an anisotropic substrate with controlled pre-tilt angle more than two degrees.

In some embodiments, the substrate is coated by anisotropic liquid crystal material. In some embodiments, the substrate is coated by polyamide like material with additional patterning and rubbing.

In some embodiments, the cells contact the cell culture medium. By "cell culture medium," "culture medium" (plural "media" in each case) and "medium formulation" herein is meant a nutritive solution that supports the cultivation and/or growth of cells; these phrases may be used interchangeably.

By "contacting" herein is meant the placing of cells to be cultivated into a culture vessel with the medium in which the cells are to be cultivated. The term "contacting" encompasses inter alias mixing cells with medium, perfusing cells with medium, pipetting medium onto cells in a culture vessel, and submerging cells in culture medium.

There are many varied types of cell culture media that can be used to support cell viability, for example DMEM medium (H. J. Morton, In Vitro, 6, 89/1970), F12 medium (R. G. Ham, Proc. Natl. Acad. Sci. USA, 53, 288/1965) and RPM1 1640 medium (J. W. Goding, J. Immunol. Methods, 39, 285/1980; JAMA 199, 519/1957). Such media (often called "basal media"), however, are usually seriously deficient in the nutritional content required by most animal cells. Often, serum must be added to the basal media to overcome these deficiencies. Generally, fetal bovine serum (FBS), horse serum or human serum is used in significant concentrations.

While the use of FBS is desirable, and often necessary, for proper cell growth, it has several disadvantages. It is relatively expensive, and its use greatly increases the cost of cell culture. In addition, it is difficult to obtain serum with consistent growth characteristics. Further, the biochemical complexity of FBS can complicate the downstream processing of the proteins of interest, therefore raising the production costs.

Serum-free medium is an excellent alternative to standard serum-containing media for the cultivation of cells. It has several advantages, which include better definition of the composition, reduced contamination and lower cost. A scrum-free medium having cultivation ability comparable to that of the conventional serum-containing medium has long been sought.

One strategy to develop serum-free media has been to supplement the basal media with appropriate nutrients to avoid the addition of FBS, without sacrificing cell growth and/or protein production. Examples of such components include bovine serum albumin (BSA) or human serum albumin (HSA); certain growth factors derived from natural (animal) or recombinant sources, including epidermal growth factor (EGF) or fibroblast growth factor (FGF); lipids such as fatty acids, sterols and phospholipids; lipid derivatives and complexes such as phosphoethanolamine, ethanolamine and lipoproteins; protein and steroid hormones such as insulin, hydrocortisone and progesterone; nucleotide precursors; and certain trace elements. See Cell Culture Methods for Molecular and Cell Biology, Vol. 1, Barnes, D. W., et al., eds., New York: Alan R. Liss, Inc., (1984), herein incorporated by reference in its entirety.

B. Scaffolds with Oriented Collagen

In another aspect, the present invention provides scaffolds with oriented collagen, such as scaffolds with linear pattern collagen materials formed thereon.

In one aspect, the present invention provides a three-dimensional matrix for use in three-dimensional cell culture, said matrix comprises a collagen layer, wherein said collagen layer comprises a plurality of crimped fibrils with at least one preferred orientation, and wherein said collagen layer has a uniaxial orientation.

In some embodiment, the collagen layer is prepared by shearing and drying on an anisotropic substrate with controlled pre-tilt angle. In some embodiments, the substrate is coated by anisotropic liquid crystal material. In some embodiments, the substrate is coated by polyamide like material with additional patterning and rubbing.

In some embodiments, linear pattern collagen layers of the present invention are used in cell culture to provide a platform or guidance for growing cells and optionally may increase their proliferation rate. There is a strong evidence that oriented collagen layer provide a guidance for growing cells and increase their proliferation rate. In the paper Yoshizato K. et al., Growth and Differ., 23 (2), 175-184 (1981), a collagen film in which the collagen fibers were aligned was prepared and characterized by scanning electron microscopy. Cell orientation on this film was studied in vitro using human fibroblasts and chick embryo myoblasts. Ninety-four percent of innoculated fibroblasts were aligned along the direction of the collagen fiber. The myoblasts showed a similar alignment along the direction of collagen fiber. Myoblast fusion was accelerated on the aligned membrane as compared to a randomly oriented film, suggesting some role of contact guidance in muscle cell differentiation.

In one aspect, the present invention provides a collagen structure that mimics the preferred environment of proliferating stem cells, where the direction of the collagen fiber orientation acts a barrier to prevent the loss of stem cells from the niche.

In some embodiment, the invention provides a scaffold or layer with linear pattern collagen layer(s) formed thereon for growing stem cell. By "stem cell" herein is meant cells of multi-cell organisms that are capable of retaining the ability to reinvigorate themselves through mitotic cell division and can differentiate into a diverse range of specialized cell types. There are two broad types of mammalian stem cells. Embryonic stem cells that are found in blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin or intestinal tissues.

In some embodiments, the oriented collagen provided herein is used in tissue engineering. Different forms of collagen are the most important materials of tissue engineering. They are widely used for healing of burn wounds, artificial nerve construction, regeneration of damaged heart tissue, etc. Since the extra cellular matrix of the human body has a well oriented structure which changes with age and human condition, G. Avtandilov et al., Journal of Applied Crystallography, 33:511-514 (2000); P. Lazarev et al., Annual International Conference of the IEEE Engineering in Medicine and Biology—Proceedings; 2000; v.4, p. 3230-3233; Cuttle, L et al., Wound Repair and Regeneration, 13:198-204 (2005), researchers have tried to mimic this structure.

C. Collagen Clinical Applications

The preparation of collagen for use as a biomaterial can be broadly classified into two major approaches. In one approach, biological structures are treated in some way to remove noncollagenous materials and to strengthen the remaining collagen. The existing structure, and probably many of the intermolecular crosslinkages, are retained. In the second approach, collagen is first solubilized and purified, and then attempts are made to re-form and re-crosslink the material in the proper shape. The former approach has the advantage of exploiting normal, biological, three-dimensional structure in a biomaterial, but has the disadvantage of having relatively fixed and predetermined configurations. The latter approach has had the problem of reconstituting collagen materials with appropriate strength, but offers a very broad potential in possible applications.

The success of collagen heterografts indicates, among other things, that clinically significant antigenicity is generally not a problem. One of the most completely studied structures has been the collagen arterial graft of bovine origin, produced by Johnson and Johnson.

Reconstituted collagen would seem to have a greater potential for biomaterials. Reconstituted collagen can be purified, its structure defined, side groups altered, and any type of biomedical device designed. The major medical applications to date have been extruded collagen fibers, collagen membranes, collagen gels, and collagen sponges.

In another aspect, the present invention provides a oriented collagen coated graft on which stem cells are seeded and daughter cells of stem cells are induced to differentiate into the selected type of cell. Such graft is used as tissue graft or artificial organ. The desired phenotype of the cells can be induced with a combination of chemical physical factors different from those that maintain stem cells as known in the art. For example, often the daughter cells that will undergo differentiation migrate away from the stem cell niche. In some embodiments, the present invention provides a collagen structure comprising linear pattern collagen. Such structure can be used to promote the migration of the daughter cells, with surface orientation acting as a guide.

Some cells, such as fibroblasts in connective tissues like skin, bone, and tendon, are capable of division into two differentiated daughter cells if necessary to heal a wound. In some embodiments, the present invention provides cell-seeded graft, and the graft comprises a collagen layer with linear pattern. By "graft" herein is meant cells, tissues, or organs that can be transplanted to a subject in need of such graft. For example a graft can be skin tissues.

The cell-seeded grafts, including those derived from stem cells, must be immune-compatible with the host. Thus, ideally, the stem cells used in making the grafts should be from the same subject that accepts such grafts. For example, the stem cells, such as those collected from donor's biblical cord blood and saved can later be used to provide stem cells for graft seeding. Alternatively, stem cells may be generated by differentiated cells of the subject itself by genetic reprogramming. Alternatively, a databank can be searched for match donors, such as done for marrow grafts.

In another aspect, the present invention provide clinical grafts with linear scaffold orientation, such as artificial tendon and ligament grafts. Tendon and ligaments can be ruptured by forces exceeding their strength (Achilles tendon, cruciate ligament), fail due to insufficient blood supply (rotator cuff), or suffer penetrating trauma (foot, arm, and hand tendon). Collagen makes up 70% or more of the wet weight of tendons and ligaments. See FIG. 8B.

In some embodiments, the present invention provides a pre-fabricated, cell-seeded tendon graft based on a highly aligned collagen substrate as provided herein. The graft can be made using adult differentiated fibroblast and vascular cells harvested from skin or other less critical connective tissues. Such graft does not need to use stem cells, thus is much easier to produce.

In some embodiments, the oriented collagen is used in a would healing process. During the wound healing process, oriented collagen acts to modulate cell proliferation and migration and is important in the wound contraction process. Cuttle L., et al., Wound Repair and Regeneration, 13:198-204 (2005). The patterns of collagen deposition in healing fetal and adult wounds differ markedly. Fetal skin regenerates collagen fibers in neat, well-organized patterns with close to perfect tissue architecture, whereas postnatal and adult skin heals with collagen laid down in thick disorganized patterns and scar formation. Colwell A S et al., Front Biosci; 8:s1240-8 (2003). The scarless healing properties of fetal skin are lost in many animal models in late gestation. Further evidence of importance of collagen structure for scarless wound healing was presented in Goffin, A J., et al., Oriented Collagen Films for Wound-Healing Applications, 2006, Annual Meeting, Society for Biological Engineering.

In some embodiments, the collagen films provided herein are used to prevent adhesions following tendon injuries, to lengthen levator palpebrae muscles ophthalmic surgery, and to repair transected nerves. Aparray & Tanner reported the successful use of collagen film in treating corneal burns. Prudden & Wolarsky have used collagen prepared from enzyme-treated bovine cartilage to enhance wound healing. They found that this preparation reversed steroid induced inhibition of wound healing.

Collagen films provided herein may further be used for burn dressings and wound healing. In some embodiments, the collagen is preferably not heavily cross-linked. If the films are heavily cross-linked, they do not become incorporated into the tissue, but rather, granulation, and re-epithelialization take place beneath the films. Here the film acts as an inert dressing. Collagen felt or sponge, on the other hand, may function as a true artificial skin. Healing of bone defects and wounds also appears enhanced by collagen.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

EXAMPLES

The following examples are provided for illustration purposes only, and are not intended to limit the scope of the present invention in any way.

Example 1

Bioassay of Cell Sensitivity to Collagen Orientation

New cell lines are developed for research and for human therapeutic implantation. While the ability of different cell types to bind to and assume a shape dependent on orientation or microtexture of the substrate on which they grow is generally known, cloning, genetic modification and similar manipulation of cells may alter this ability. For example, fibroblasts bind and orient on a collagen surface by means of cell-surface receptors, while lymphocytes do not bind but interact with collagen by insertion of pseudopodia between collagen fibrils.

In order to test an unknown cell for ability to bind and orient, aliquots of cells suspended in culture medium are deposited onto a selection of glass slides or "chips" coated with randomly-oriented or unidirectionally-oriented collagen of increasing thickness or depth of texture (grooves between collagen fibrils). Alternatively, a single slide having a thickness or depth gradient may replace a series of separate slides. The collagen coatings will have been previously characterized by culture of a reference cell population having known interaction with oriented surfaces.

The unknown cells will be cultured, typically for three or four days, in an appropriate medium (for example, Dulbecco's Minimum Essential Medium+10% fetal bovine serum+ 1% glutamine/antibiotics) at pH 7 and 37° C. in an humidified incubator. After 24 hours, take 20×-40× microphotographs (min 3 fields/specimen) to show both adherent and detached cells. Pipet off culture medium; count detached cells in Coulter counter or hemocytometer. Repeat photos of same fields to show only adherent cells. Replace 3.5 ml fresh medium (without cells). After 3 days, fix by pipeting off culture medium and adding 10% buffered neutral formalin. Stain with hematoxylin-eosin or other histologic stain, mount coated side DOWN on 1×3 inch microscope slides or coated side UP for scanning electron or atomic force microscopy.

Analyze ratio of attached to floating cells and dimensions of cells (i.e.: elongation in direction of substrate orientation) using "NIH Image" or similar software.

Similar bioassays can be used to evaluate cell interaction with non-collagenous factors coated onto the collagen layer.

Example 2

Fabrication of a Tendon or Ligament Graft

When surgical repair to damaged tendons and ligaments is necessary, donor tissue is in short supply. The ideal graft is taken from another joint in the patient's body (autograft), but at the expense of pain and loss of function at the donor site. Cadaver or synthetic grafts can often be an adequate substitute, even though living cells within the graft are absent.

To fabricate such a graft using oriented collagen coated onto glass slides as a starting material, the dry coating is mechanically detached at one end of the slide and peeled off in a single sheet (other means for detaching the coating are described in separate patents). An interlocking crimped or helical ultrastructure (quaternary molecular structure) aids in maintaining the integrity of the collagen sheet both in processing and later functioning within the body; tensile loads are transferred laterally via interlocking regions of adjacent fibrils so that the device behaves as if fibrils are continuous for its entire length even when composed of shorter fibrils.

The process of peeling results in spontaneous rolling of the width of the collagen strip about its long axis (the dominant orientation axis). If more control over the macro-geometry is desired, the collagen sheet or multiple sheets can be wrapped about a cylindrical mandrel which is later withdrawn; this method allows multiple layers to be oriented at various angles to the axis of the whole tendon.

Surgical implantation of the device employs the same procedure as autograft tendon or ligament. Where a flat ligament or large tendon is to be replaced, the surgeon can implant several thin cylindrical grafts side-by-side, or this assembly can be pre-fabricated with a smooth outer layer for better sliding in the tendon sheath.

Example 3

Fabrication of a Viable Cell-seeded Tendon or Ligament Graft

To more closely approximate a tendon or ligament autograft, the oriented collagen graft described above can first be seeded with cells extracted from a tissue biopsy taken from the patient's skin. Skin fibroblasts are separated from other cells and deposited onto collagen-coated slides. An advantage of this method is that the relatively few cells typically obtained from a biopsy specimen can proliferate directly on the membrane on which they will be implanted into the body, instead of requiring separate proliferation and transfer steps.

When the cells have reached the desired density, the collagen sheet is detached from the slide and rolled into a tube, taking care that the cells are not mechanically damaged, contaminated or allowed to dry. Multi-layer tubes or side-by-side bundles of cell-containing tubes may be fabricated as described above.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

Example 4

The Making of the Collagen Layer

Experiments were performed using various types of collagens. It is useful to describe an example of the process to produce two types of oriented collagen matrix. Rat tail, Type I collagen is provided by BD BioSciences at a concentration of 10.6 mg/ml. This "raw" collagen is concentrated by any one of a number of techniques such as dialysis with PEG, microfiltration centrifuge or vacuum centrifuge. The concentration process is carried out at 4 degrees celcius. Collagen concentrated to 20 mg/ml is coated onto a glass substrate using a flat surface positioned 10 microns above the glass surface and moving at a velocity of approximately 20 mm/second. The shear stresses on the collagen film trapped between the glass substrate and moving flat surface create an oriented matrix structure that is "woven" in appearance. It contains a plurality of approximately circular domains made up of individual collagen fibrils oriented substantially parallel to one another. When the concentration is increased to 30 mg/ml, the resultant matrix structure is "uniaxial" in appearance as described in this patent.

Similar processes are used to create woven and uniaxial collagen matrices using bovine and human collagen. Lower concentration produces woven while higher concentration produces uniaxial orientation. An additional orientation can be produced by a rubbing of the surface of the substrate. The types of collagen and parameters of the experiments are summarized in Table I

TABLE 1

| Collagen source | | rat tail | rat tail | bovine | human |
|---|---|---|---|---|---|
| Collagen type | | Type I | Type I | Type I | Type I |
| Substrate | | glass | glass | glass | |
| Initial "concentration" (mg/ml) | mg/ml | 10.6 | 10.6 | 6.5 | 3 |
| Final "concentration" (mg/ml) | mg/ml | 29 | 20 | 19 | 26 |
| Gap between substrate and flat face of coating head | micron | 10 | 10 | 10 | 10 |
| Coating velocity | mm/sec | 20 | 70 | 20 | 20 |
| Result | | uniaxial | woven | uniaxial | uniaxial |

All patents, patent applications, publications, and references cited herein are expressly incorporated by reference to the same extent as if each individual publication or patent application was specifically and individually indicated to be incorporated by reference.

What is claimed is:

1. A monolayer or multilayer stack comprising a collagen layer, wherein said collagen layer comprises a plurality of crimped fibrils with at least one preferred orientation, and wherein said collagen layer has a uniaxial orientation.

2. The monolayer or multilayer stack according to claim 1, wherein said collagen layer is formed by fibrils of at least one type of collagens: I, II, III, V, or XI.

3. The monolayer or multilayer stack according to claim 1, wherein said plurality of crimped fibrils form a crimped fibril assembly, and wherein said assembly comprises a plurality of ridges and valleys.

4. The monolayer or multilayer stack according to claim 3, wherein said plurality of crimped fibrils forms a repeatable elongated pattern consisting of an alternating series of ridges and valleys aligned in one preferred direction.

5. The monolayer or multilayer stack according to claim 3, wherein said plurality of crimped fibrils forms a repeatable elongated pattern consisting of an alternating series of ridges and valleys aligned in two preferred directions.

6. The monolayer or multilayer stack according to claim 4 or 5, wherein an alternating series of ridges and valleys have a pitch in range 100 nm-10 micron.

7. The monolayer or multilayer stack according to claim 4 or 5, wherein said ridges and valleys have width in range 50 nm-5 micron and length in range 100 nm-50 micron.

8. The monolayer or multilayer stack according to claim 4 or 5, wherein an alternating series of ridges and valleys have depth in range 10 nm-1 micron.

9. The monolayer or multilayer stack according to claim 4 or 5, wherein the fibrils composing the ridges have an opposite direction in adjacent ridges.

10. The monolayer or multilayer stack according to claim 5, wherein an angle between two preferred directions of an alternating series of ridges and valleys is in range 40-180 degree.

11. The monolayer or multilayer stack according to claim 1, wherein the angle between said uniaxial orientation and said preferred orientation is from 0 to 30 degrees.

12. The monolayer or multilayer stack according to claim 1, wherein said crimped fibrils display at least a partial translational order that correlates to said preferred orientation.

13. The monolayer or multilayer stack according to claim 1, wherein said crimped fibrils do not display at least a partial translational order that correlates to said preferred orientation.

14. The monolayer or multilayer stack according to claim 3, wherein said crimped fibrils are helical-like fibrils, and wherein upper helixes of said helical-like fibers form said ridges and the lower helixes of said helical-like fibers form said valleys.

15. The monolayer or multilayer stack according to claim 1, wherein the alignment angle variation of said crimped fibrils is less than ±15°.

16. The monolayer or multilayer stack according to claim 1, wherein the topography of a surface of said collagen layer exhibits Fourier frequency content containing at least two peaks.

17. The monolayer or multilayer stack according to claim 3, wherein the topography of a surface of said collagen layer exhibits one dimensional Fourier frequency content which produces at least one peak when measured substantially orthogonally to the preferred direction of the ridges.

18. The monolayer or multilayer stack according to claim 2, wherein the at least one type of collagen may be biologically or chemically modified.

19. The monolayer or multilayer stack according to claim 1, wherein there are at least 10 aligned crimped fibrils per 50 μm wide area of said collagen layer.

20. The monolayer or multilayer stack according to claim 1, wherein the cross section of said crimped fibrils is at least 30 nm.

21. The monolayer or multilayer stack according to claim 1, wherein the length of said crimped fibrils is at least 2 μm.

22. The monolayer or multilayer stack according to claim 3, wherein the average distance between adjacent ridges of said crimped fibril assembly is at least 100 nm.

23. The monolayer or multilayer stack according to claim 3, wherein said valley is about 10 to 1000 nm deep.

24. The monolayer or multilayer stack according to claim 1, wherein the surface topography of said collagen layer exhibits an anisotropic Fourier image containing at least two petals.

25. The monolayer or multilayer stack according to claim 1, wherein said collagen layer produces anisotropic transmission diffraction pattern containing at least two petals when exposed to a collimated monochromatic light source having visible wavelength.

26. The monolayer or multilayer stack according to claim 1, wherein said collagen layer produces anisotropic reflective diffraction pattern containing at least two petals when exposed to a collimated monochromatic light source having visible wavelength.

27. The monolayer or multilayer stack according to claim 4, wherein said ridges formed by the upper helixes of said helical-like fibers form an angle of at least 30 degree with said preferred orientation.

28. The monolayer or multilayer stack according to claim 1, comprises at least two collagen layers, wherein said uniaxial direction of each collagen layer may not necessarily be parallel to each another.

29. The monolayer or multilayer stack according to claim 1, wherein said collagen layer further comprises pit-like formation at the boundaries of said crimped fibrils, and wherein said pit-like formations are filled with any one of: hydrogels, peptide based biomaterials, living tissue cell, and other bioactive materials like the incorporated ligands, encapsulated DNA, and growth factors, or the combinations thereof.

30. The monolayer or multilayer stack according to claim 1, further comprises metal nanowires or carbon nanotubes.

31. The monolayer or multilayer stack according to claim 1, further comprises at least one functional layer.

32. The monolayer or multilayer stack according to claim 31, wherein said functional layer is selected from any one of: lipid membrane, coagulant, living tissue cell layer, adhesion promotion layer, carrier layer, protective layer, delaminating promotion layer, or combinations thereof.

33. The monolayer or multilayer stack according to claim 1, wherein said collagen layer is made by a liquid film applicator comprising:
  (i) at least two longitudinal side members having the form of parallel wedge-like rails with their bases occurring in the same plane as the substrate;
  (ii) a crossover member having the form of a bridge between said side members, wherein said crossover member has at least one flat face and is in contact with each said rail in at least one point; and
  (iii) a clamp system ensuring strict fixation of the bridge at any preset position on said rails, wherein said bridge can be moved along both said rails so that the flat face of said bridge makes a certain constant dihedral angle within 0-10 are minutes with the substrate plane and the gap between said flat face and said substrate plane has a width from 5 to 50 micron.

34. The monolayer or multilayer stack according to claim 1, wherein said collagen layer is made by the steps of:
  conveying a collagen solution to a first plate and a second plate, wherein said second plate is held substantially parallel to said first plate at a gap width of 5 to 500 microns, and wherein the collagen solution is captured between said first and second plates; and moving said second plate parallel to said first plate to generate suitable shearing force on said collagen solution to produce said collagen layer, wherein said first plate being held stationary during said moving step, and wherein the direction of moving the second plate is the coating direction.

35. The monolayer or multilayer stack according to claim 34, wherein the coating direction is parallel to said uniaxial direction.

36. The monolayer or multilayer stack according to claim 34, wherein the concentration of said collagen solution is about 10 mg/ml-30 mg/ml.

37. The monolayer or multilayer stack according to claim 34, wherein the concentration of said collagen solution is at least 25 mg/ml.

38. The monolayer or multilayer stack according to claim 34, wherein said collagen solution presents in a nematic liquid crystal state.

39. The monolayer or multilayer stack according to claim 1, wherein said collagen layer is made by shearing of concentrated liquid collagen solution.

40. The monolayer or multilayer stack according to claim 1, wherein said collagen layer is made by shearing of concentrated liquid collagen solution having at least one of the collagen types of I, II, III, VI and XI, and optionally having an additive that is capable of promoting orientation or adhesion of said collagen.

41. The monolayer or multilayer stack according to claim 1, wherein said additive is ATP.

42. The monolayer or multilayer stack according to claim 1, wherein said collagen layer further comprises cross-links by intra-monomeric disulfide bridges, glycosydic cross-links formed via nonenzymatic glycation, interstitial phosphate or sulfate cross-links, or covalent linkages promoted by the activity of the enzyme lysyl oxidase.

43. A three-dimensional matrix for use in three-dimensional cell culture, said matrix comprises a collagen-based layer according to claim 1.

44. The three dimensional matrix according to claim 43, wherein the collagen layer is prepared by shearing and drying on an anisotropic substrate with controlled pre-tilt angle.

45. The three-dimensional matrix according to claim 43, wherein said substrate is coated by anisotropic liquid crystal material.

46. The three-dimensional matrix according to claim 43, wherein said substrate is coated by polyamide like material with additional patterning and rubbing.

47. A graft comprising a collagen layer, wherein said collagen-layer is according to claim 1.

48. The graft according to claim 47, wherein said graft is a tendon graft or a ligament graft.

49. The graft according to claim 47, further comprises a plurality of fibroblasts deposited on said collagen layer.

* * * * *